US009681891B2

(12) United States Patent
Andreas et al.

(10) Patent No.: US 9,681,891 B2
(45) Date of Patent: Jun. 20, 2017

(54) TYMPANOSTOMY TUBE DELIVERY DEVICE WITH CUTTING DILATOR

(71) Applicant: Tusker Medical, Inc., Menlo Park, CA (US)

(72) Inventors: Bernard H. Andreas, Redwood City, CA (US); T. Daniel Gross, Los Gatos, CA (US); Matthew D. Clopp, Santa Clara, CA (US); Arkady Kokish, Los Gatos, CA (US)

(73) Assignee: Tusker Medical, Inc., Menlo Park, CA (US)

( * ) Notice: Subject to any disclaimer, the term of this patent is extended or adjusted under 35 U.S.C. 154(b) by 943 days.

(21) Appl. No.: 13/804,612

(22) Filed: Mar. 14, 2013

(65) Prior Publication Data

US 2014/0277050 A1 Sep. 18, 2014

(51) Int. Cl.
*A61B 17/34* (2006.01)
*A61F 11/00* (2006.01)
*A61B 17/00* (2006.01)

(52) U.S. Cl.
CPC ........ *A61B 17/3468* (2013.01); *A61F 11/002* (2013.01); *A61B 2017/00477* (2013.01)

(58) Field of Classification Search
CPC ............ A61B 17/3417; A61B 17/3468; A61B 2017/3454; A61B 2017/346; A61F 11/002
See application file for complete search history.

(56) References Cited

U.S. PATENT DOCUMENTS

| 858,673 | A | 7/1907 | Roswell |
|---|---|---|---|
| 1,920,006 | A | 7/1933 | Dozier et al. |
| 2,162,681 | A | 6/1939 | Ryan |
| 3,473,170 | A | 10/1969 | Haase et al. |
| 3,638,643 | A | 2/1972 | Hotchkiss |
| 3,741,197 | A | 6/1973 | Sanz et al. |

(Continued)

FOREIGN PATENT DOCUMENTS

| CN | 86105171 A | 3/1987 |
|---|---|---|
| DE | 19618585 | 11/1997 |

(Continued)

OTHER PUBLICATIONS

U.S. Appl. No. 13/804,553, filed Mar. 14, 2013.

(Continued)

*Primary Examiner* — Sarah W Aleman

(57) ABSTRACT

A tympanostomy tube delivery device comprises a body, a cannula extending distally from the body, and a cylindraceous member disposed within the cannula. The cylindraceous member comprises a tubular portion and a plurality of leaves positioned at the distal end of the tubular portion. The leaves are movable between a collapsed position and an expanded position. The cylindraceous member is slidable relative to the cannula to selectively expose the leaves relative to the open distal end of the cannula. A first leaf of the plurality of leaves has a sharp distal point configured to pierce a tympanic membrane and a longitudinally extending sharp edge. The cylindraceous member may be used to create and dilate a myringotomy incision in a tympanic membrane. The tympanostomy tube delivery device may then be used to deploy a tympanostomy tube through the myringotomy incision.

20 Claims, 21 Drawing Sheets

(56) References Cited

U.S. PATENT DOCUMENTS

| | | |
|---|---|---|
| 3,807,404 A | 4/1974 | Weissman et al. |
| 3,888,258 A | 6/1975 | Akiyama |
| 3,897,786 A | 8/1975 | Garnett et al. |
| 3,913,584 A | 10/1975 | Walchle et al. |
| 3,948,271 A | 4/1976 | Akiyama |
| 3,991,755 A | 11/1976 | Vernon et al. |
| 4,168,697 A | 9/1979 | Cantekin |
| 4,335,713 A | 6/1982 | Komiya |
| 4,335,715 A | 6/1982 | Kirkley |
| 4,380,998 A | 4/1983 | Kieffer, III et al. |
| 4,468,218 A | 8/1984 | Armstrong |
| 4,473,073 A | 9/1984 | Darnell |
| 4,564,009 A | 1/1986 | Brinkhoff |
| 4,712,537 A | 12/1987 | Pender |
| 4,796,624 A | 1/1989 | Trott et al. |
| 4,800,876 A | 1/1989 | Fox et al. |
| 4,913,132 A | 4/1990 | Gabriel |
| 4,946,440 A | 8/1990 | Hall |
| 4,968,296 A | 11/1990 | Ritch et al. |
| 4,971,076 A | 11/1990 | Densert et al. |
| 5,026,378 A | 6/1991 | Goldsmith, III |
| 5,044,373 A | 9/1991 | Northeved et al. |
| 5,047,007 A | 9/1991 | McNichols et al. |
| 5,053,040 A | 10/1991 | Goldsmith, III |
| 5,092,837 A | 3/1992 | Ritch et al. |
| 5,107,861 A | 4/1992 | Narboni |
| 5,135,478 A | 8/1992 | Sibalis |
| 5,178,623 A | 1/1993 | Cinberg et al. |
| 5,254,120 A | 10/1993 | Cinberg et al. |
| 5,261,903 A | 11/1993 | Dhaliwal et al. |
| D352,780 S | 11/1994 | Glaeser et al. |
| 5,370,656 A | 12/1994 | Shevel |
| 5,421,818 A | 6/1995 | Arenberg |
| 5,466,239 A | 11/1995 | Cinberg et al. |
| 5,489,286 A | 2/1996 | Cinberg et al. |
| 5,496,329 A | 3/1996 | Reisinger |
| D378,611 S | 3/1997 | Croley |
| 5,610,988 A | 3/1997 | Miyahara |
| 5,643,280 A | 7/1997 | Del Rio et al. |
| 5,645,584 A | 7/1997 | Suyama |
| 5,658,235 A | 8/1997 | Priest et al. |
| 5,674,196 A | 10/1997 | Donaldson et al. |
| 5,676,635 A | 10/1997 | Levin |
| 5,681,323 A | 10/1997 | Arick |
| D387,863 S | 12/1997 | Herman et al. |
| 5,707,383 A | 1/1998 | Bays et al. |
| 5,775,336 A | 7/1998 | Morris |
| 5,782,744 A | 7/1998 | Money |
| 5,792,100 A | 8/1998 | Shantha |
| 5,827,295 A | 10/1998 | Del Rio et al. |
| 5,893,828 A | 4/1999 | Uram |
| 5,893,837 A | 4/1999 | Eagles et al. |
| 5,984,930 A | 11/1999 | Maciunas et al. |
| D418,223 S | 12/1999 | Phipps et al. |
| D420,741 S | 2/2000 | Croley |
| 6,022,342 A | 2/2000 | Mukherjee |
| 6,024,726 A | 2/2000 | Hill |
| 6,039,748 A | 3/2000 | Savage et al. |
| 6,045,528 A | 4/2000 | Arenberg et al. |
| D424,197 S | 5/2000 | Sydlowski et al. |
| 6,059,803 A | 5/2000 | Spilman |
| D426,135 S | 6/2000 | Lee |
| 6,077,179 A * | 6/2000 | Liechty, II ............ F42B 6/08 473/582 |
| 6,110,196 A | 8/2000 | Edwards |
| 6,137,889 A | 10/2000 | Shennib et al. |
| 6,171,236 B1 | 1/2001 | Bonutti |
| 6,183,469 B1 | 2/2001 | Thapliyal et al. |
| 6,200,280 B1 | 3/2001 | Brenneman et al. |
| 6,206,888 B1 | 3/2001 | Bicek et al. |
| 6,245,077 B1 | 6/2001 | East et al. |
| 6,251,121 B1 | 6/2001 | Saadat |
| 6,258,067 B1 | 7/2001 | Hill |
| D450,843 S | 11/2001 | McGuckin, Jr. et al. |
| 6,358,231 B1 | 3/2002 | Schindler et al. |
| 6,398,758 B1 | 6/2002 | Jacobsen et al. |
| 6,440,102 B1 | 8/2002 | Arenberg et al. |
| 6,447,522 B2 | 9/2002 | Gambale et al. |
| 6,475,138 B1 | 11/2002 | Schechter et al. |
| 6,512,950 B2 | 1/2003 | Li et al. |
| 6,514,261 B1 | 2/2003 | Randall et al. |
| 6,520,939 B2 | 2/2003 | Lafontaine |
| 6,522,827 B1 | 2/2003 | Loeb et al. |
| 6,553,253 B1 | 4/2003 | Chang |
| 6,645,173 B1 | 11/2003 | Liebowitz |
| 6,648,873 B2 | 11/2003 | Arenberg et al. |
| 6,663,575 B2 | 12/2003 | Leysieffer |
| 6,682,558 B2 | 1/2004 | Tu et al. |
| 6,770,080 B2 | 8/2004 | Kaplan et al. |
| 6,916,159 B2 | 7/2005 | Rush et al. |
| 6,962,595 B1 | 11/2005 | Chamness et al. |
| 7,127,285 B2 | 10/2006 | Henley et al. |
| 7,137,975 B2 | 11/2006 | Miller et al. |
| D535,027 S | 1/2007 | James et al. |
| 7,160,274 B2 | 1/2007 | Ciok et al. |
| 7,344,507 B2 | 3/2008 | Briggs et al. |
| 7,351,246 B2 | 4/2008 | Epley |
| 7,381,210 B2 | 6/2008 | Zarbatany et al. |
| D595,410 S | 6/2009 | Luzon |
| 7,563,232 B2 | 7/2009 | Freeman et al. |
| D598,543 S | 8/2009 | Vogel et al. |
| 7,654,997 B2 | 2/2010 | Makower et al. |
| 7,677,734 B2 | 3/2010 | Wallace |
| 7,704,259 B2 | 4/2010 | Kaplan et al. |
| 7,749,254 B2 | 7/2010 | Sobelman et al. |
| D622,842 S | 8/2010 | Benoist |
| D640,374 S | 6/2011 | Liu et al. |
| 8,052,693 B2 | 11/2011 | Shahoian |
| 8,192,420 B2 | 6/2012 | Morriss et al. |
| 8,249,700 B2 | 8/2012 | Clifford et al. |
| 8,282,648 B2 * | 10/2012 | Tekulve ............ A61B 17/8811 604/164.11 |
| 8,409,175 B2 | 4/2013 | Lee et al. |
| 8,425,488 B2 | 4/2013 | Clifford et al. |
| 8,498,425 B2 | 7/2013 | Graylin |
| 8,518,098 B2 | 8/2013 | Roeder et al. |
| 8,702,722 B2 | 4/2014 | Shahoian |
| 8,840,602 B2 | 9/2014 | Morriss et al. |
| 8,849,394 B2 | 9/2014 | Clifford et al. |
| 8,864,774 B2 | 10/2014 | Liu et al. |
| 8,998,927 B2 | 4/2015 | Kaplan et al. |
| 9,011,363 B2 | 4/2015 | Clopp et al. |
| 9,023,059 B2 | 5/2015 | Loushin et al. |
| 9,216,112 B2 | 12/2015 | Clifford et al. |
| 9,320,652 B2 | 4/2016 | Andreas et al. |
| 9,387,124 B2 | 7/2016 | Clifford |
| 2001/0020173 A1 | 9/2001 | Klumb et al. |
| 2002/0026125 A1 | 2/2002 | Leysieffer |
| 2002/0069883 A1 | 6/2002 | Hirchenbain |
| 2002/0111585 A1 | 8/2002 | Lafontaine |
| 2002/0138091 A1 | 9/2002 | Pflueger |
| 2002/0161379 A1 | 10/2002 | Kaplan et al. |
| 2002/0169456 A1 | 11/2002 | Tu et al. |
| 2003/0018291 A1 | 1/2003 | Hill et al. |
| 2003/0040717 A1 | 2/2003 | Saulenas et al. |
| 2003/0060799 A1 | 3/2003 | Arenberg et al. |
| 2003/0187456 A1 | 10/2003 | Perry |
| 2003/0199791 A1 | 10/2003 | Boecker et al. |
| 2004/0054339 A1 | 3/2004 | Ciok et al. |
| 2005/0033343 A1 | 2/2005 | Chermoni |
| 2005/0165368 A1 | 7/2005 | Py et al. |
| 2005/0182385 A1 | 8/2005 | Epley |
| 2005/0187546 A1 | 8/2005 | Bek et al. |
| 2005/0235422 A1 | 10/2005 | Wallace |
| 2005/0240147 A1 | 10/2005 | Makower et al. |
| 2006/0095050 A1 | 5/2006 | Hartley et al. |
| 2006/0142700 A1 | 6/2006 | Sobelman et al. |
| 2006/0155304 A1 | 7/2006 | Kaplan et al. |
| 2006/0161218 A1 | 7/2006 | Danilov |
| 2006/0163313 A1 | 7/2006 | Larson |
| 2006/0282062 A1 | 12/2006 | Ishikawa et al. |
| 2007/0233222 A1 | 10/2007 | Roeder et al. |
| 2008/0027423 A1 | 1/2008 | Choi et al. |
| 2008/0051804 A1 | 2/2008 | Cottler et al. |

(56) References Cited

U.S. PATENT DOCUMENTS

| | | |
|---|---|---|
| 2008/0212416 A1 | 9/2008 | Polonio et al. |
| 2008/0262468 A1 | 10/2008 | Clifford et al. |
| 2008/0262508 A1 | 10/2008 | Clifford et al. |
| 2008/0262510 A1 | 10/2008 | Clifford |
| 2009/0163828 A1 | 6/2009 | Turner et al. |
| 2009/0209972 A1 | 8/2009 | Loushin et al. |
| 2009/0299344 A1 | 12/2009 | Lee et al. |
| 2009/0299379 A1 | 12/2009 | Katz et al. |
| 2010/0041447 A1 | 2/2010 | Graylin |
| 2010/0061581 A1 | 3/2010 | Soetejo et al. |
| 2010/0198135 A1 | 8/2010 | Morriss et al. |
| 2010/0217296 A1 | 8/2010 | Morriss et al. |
| 2010/0324488 A1 | 12/2010 | Smith |
| 2011/0015645 A1 | 1/2011 | Liu et al. |
| 2011/0022069 A1 | 1/2011 | Mitusina |
| 2011/0077579 A1 | 3/2011 | Harrison et al. |
| 2011/0288559 A1 | 11/2011 | Shahoian |
| 2012/0179187 A1 | 7/2012 | Loushin et al. |
| 2012/0265097 A1 | 10/2012 | Melchiorri et al. |
| 2012/0310145 A1 | 12/2012 | Clifford et al. |
| 2013/0090544 A1 | 4/2013 | Clifford et al. |
| 2013/0338678 A1 | 12/2013 | Loushin et al. |
| 2014/0094733 A1 | 4/2014 | Clopp et al. |
| 2014/0100584 A1 | 4/2014 | Konstorum et al. |
| 2014/0194891 A1 | 7/2014 | Shahoian |
| 2014/0276906 A1 | 9/2014 | Andreas et al. |
| 2015/0164695 A1 | 6/2015 | Liu et al. |
| 2015/0305944 A1 | 10/2015 | Kaplan et al. |
| 2016/0038341 A1 | 2/2016 | Clopp et al. |
| 2016/0038342 A1 | 2/2016 | Van et al. |
| 2016/0045369 A1 | 2/2016 | Clopp |
| 2016/0045370 A1 | 2/2016 | Andreas et al. |
| 2016/0045371 A1 | 2/2016 | Girotra et al. |

FOREIGN PATENT DOCUMENTS

| | | | |
|---|---|---|---|
| DE | 19918288 | A1 | 10/2000 |
| EP | 0214527 | A1 | 3/1987 |
| FR | 2526656 | | 11/1983 |
| JP | H 07-116190 | A | 5/1995 |
| WO | WO 99/11175 | A1 | 3/1999 |
| WO | WO 2006/119512 | | 11/2006 |
| WO | WO 2008/030485 | | 3/2008 |
| WO | WO 2008/036368 | | 3/2008 |
| WO | WO 2008/131195 | | 10/2008 |
| WO | WO 2009/010788 | | 1/2009 |
| WO | WO 2011/008948 | | 1/2011 |
| WO | WO 2014/075949 | | 5/2014 |
| WO | WO 2014/143543 | | 9/2014 |
| WO | WO 2014/158571 | | 10/2014 |
| WO | WO 2016/022899 | | 2/2016 |
| WO | WO 2016/025308 | | 2/2016 |
| WO | WO 2016/025309 | | 2/2016 |
| WO | WO 2016/025310 | | 2/2016 |
| WO | WO 2016/025453 | | 2/2016 |

OTHER PUBLICATIONS

International Search Report and Written Opinion dated Apr. 17, 2014 for Application No. PCT/US2014/018347.
Patent Examination Report No. 1 for Australian Patent Application No. 2013209354, dated Oct. 13, 2014, 5 pages.
First Office Action for Chinese Patent Application No. 200880020861.9, dated Jul. 12, 2011, 10 pages.
Second Office Action for Chinese Patent Application No. 200880020861.9, dated Dec. 31, 2011, 3 pages.
Search Report for Chinese Patent Application No. 201310047126.X, dated Mar. 6, 2015, 2 pages.
Second Office Action for Chinese Patent Application No. 201310047126.X, dated Mar. 16, 2015, 10 pages.
Office Action for European Application No. 08746237.0, mailed Mar. 24, 2016, 3 pages.
Office Action for European Application No. 08746237.0, mailed Aug. 4, 2015, 7 pages.
Supplementary Partial Search Report for European Application No. 08746237.0, mailed Jun. 30, 2014, 9 pages.
Notification of Reasons for Refusal for Japanese Patent Application No. 2010-504267, dated Nov. 20, 2012, 4 pages.
Notification of Reasons for Refusal for Japanese Patent Application No. 2010-504267, dated Nov. 12, 2013, 4 pages.
International Search Report for International Application No. PCT/US2008/060779, mailed Sep. 3, 2008.
Written Opinion for International Application No. PCT/US2008/060779, mailed Sep. 3, 2008.
International Preliminary Report on Patentability for International Application No. PCT/US2008/060779, dated Nov. 17, 2009.
Office Action for U.S. Appl. No. 11/749,729, mailed May 26, 2011, 11 pages.
Office Action for U.S. Appl. No. 11/749,729, mailed Jun. 17, 2010, 8 pages.
Office Action for U.S. Appl. No. 11/749,733, mailed Jun. 10, 2009, 13 pages.
Office Action for U.S. Appl. No. 11/749,733, mailed Dec. 2, 2008, 9 pages.
U.S. Appl. No. 61/085,360, filed Jul. 31, 2008.
International Search Report for International Application No. PCT/US2009/052395, mailed Nov. 6, 2009.
Written Opinion for International Application No. PCT/US2009/052395, mailed Nov. 6, 2009.
International Search Report for International Application No. PCT/US2010/058718, mailed Feb. 17, 2011.
Written Opinion for International Application No. PCT/US2010/058718, mailed Feb. 17, 2011.
U.S. Appl. No. 61/225,893, filed Jul. 15, 2009.
Patent Examination Report No. 1 for Australian Application No. 2010273372, dated Nov. 12, 2014, 2 pages.
Office Action for Canadian Application No. 2,768,009, dated Aug. 4, 2016, 4 pages.
First Office Action for Chinese Application No. 201080041755.6, dated Jul. 3, 2013.
Notification of Reasons for Refusal for Japanese Application No. 2012-520778, dated Feb. 18, 2014.
Communication of the Substantive Examination Report for Mexican Application No. MX/a/2012/000691, dated Apr. 24, 2014.
International Search Report for International Application No. PCT/US2010/042128, mailed Aug. 27, 2010.
Written Opinion International Application No. PCT/US2010/042128, mailed Aug. 27, 2010.
International Preliminary Report on Patentability for International Application No. PCT/US2010/042128, dated Jan. 17, 2012.
European Search Report for European Application No. 13173409.7, mailed Sep. 16, 2013.
Search Report and Written Opinion for International Patent Application No. PCT/US2015/044179, mailed Dec. 18, 2015, 15 pages.
International Search Report and Written Opinion for International Application No. PCT/US2014/018320, mailed Jun. 2, 2014, 10 pages.
International Search Report and Written Opinion for International Application No. PCT/US2015/044173, mailed Oct. 12, 2015, 9 pages.
International Search Report and Written Opinion for International Application No. PCT/US2015/044177, mailed Oct. 30, 2015, 10 pages.
International Search Report and Written Opinion for International Application No. PCT/US2015/044183, mailed Nov. 4, 2015, 9 pages.
International Search Report and Written Opinion for International Application No. PCT/US2015/044610, mailed Nov. 5, 2015, 12 pages.
International Search Report for International Application No. PCT/US2009/069388, mailed Jun. 30, 2010.
Written Opinion for International Application No. PCT/US2009/069388, mailed Jun. 30, 2010.
Comeau, M. et al., "Local Anesthesia of the Ear by Iontophoresis," vol. 98, Arch. Otolaryngol., pp. 114-120 (Aug. 1973).

(56) References Cited

OTHER PUBLICATIONS

Comeau, M. et al., "Anesthesia of the Human Tympanic Membrane by Iontophoresis of a Local Anesthetic," The Larynogoscope, vol. 88, pp. 277-285 (1978).

Echols, D. F. et al., "Anesthesia of the Ear by Iontophoresis of Lidocaine," Arch. Otolaryngol., vol. 101, pp. 418-421 (Jul. 1975).

Epley, J. M., "Modified Technique of Iontophoretic Anesthesia for Myringotomy in Children," Arch. Otolaryngol., vol. 103, pp. 358-360 (Jun. 1977).

Hasegawa, M. et al., "Iontophorectic anaesthesia of the tympanic membrane," Clinical Otolaryngoloy, vol. 3, pp. 63-66 (1978).

Ramsden, R. T. et al., "Anaesthesia of the tympanic membrane using iontophoresis," The Journal of Laryngology and Otology, 56(9):779-785 (Sep. 1977).

"Definition of Plenum," Compact Oxford English Dictionary [online], Retrieved from the Internet: <http://oxforddictionaries.com/definition/english/plenum>, Retrieved on Aug. 6, 2012, 2 pages.

"Definition of Plenum," Merriam-Webster's Online Dictionary, 11th Edition [online], Retrieved from the Internet: <http://www.merriam-webster.com/dictionary/plenum>, Retrieved on Aug. 14, 2012, 1 page.

Medtronic XOMED, "Activent® Antimicrobial Ventilation Tubes," Rev. 1.1, pp. 1-4, 2002, Jacksonville, FL.

Micromedics Innovative Surgical Products, "Micromedics Tympanostomy Tubes," [online], Retrieved on Jul. 15, 2010, Retrieved from the Internet <URL: http://www.micromedics-usa.com/products/otology/micromedicstubes.htm>, 7 pages.

Armstrong, "A New Treatment for Chronic Secretory Otitis Media" A.M.A. Archives of Otolaryngology, pp. 653-654 (1954).

Feuerstein, "A Split-Tube Prosthesis in Serous Otitis Media" Sixty-ninth Annual Session of the American Academy of Ophthalmology and Otolaryngology, Oct. 18-23, 1964, Chicago, IL, pp. 343-344.

Jurgens. et al., "Three New Middle Ear Ventilation Tubes" Seventy-sixth Annual Session of the American Academy of Ophthalmology and Otolaryngology, Sep. 20-24, 1971, Las Vegas, NV, pp. 1017-1019 (1971).

Lindeman et al., The "Arrow Tube" Residents in Otolaryngology, Massachusetts Eye and Ear Infirmary, 1 page (1964).

Pappas, "Middle Ear Ventilation Tubes" Meeting of the Southern Section of the American Laryngological, Rhinological and Otological Society, Inc., Williamsburg, VA, Jan. 12, 1974, pp. 1098-1117.

Per-Lee, "A Wide Flanged Middle Ear Ventilation Tube" Seventy-first Annual Session of the American Academy of Ophthalmology and Otolaryngology, Oct. 16-21, 1966, Chicago, IL, pp. 358-359.

Reuter, "The Stainless Bobbin Middle Ear Ventilation Tube" Seventy-second Annual Session of the American Academy of Ophthalmology and Otolaryngology, Oct. 29-Nov. 3, 1967, Chicago, IL, pp. 121-122.

Ringenberg, "A New Middle Ear Ventilation Device" Seventy-second Annual Session of the American Academy of Ophthalmology and Otolaryngology, Oct. 29-Nov. 3, 1967, Chicago, IL, 1 page.

Schmidt et al. "Transtympanic Aeration of the Middle Ear With Blocked Eustachian Tube" Acta Otolaryng., pp. 277-282 (1965).

Sheehy, "Collar Button Tube for Chronic Serous Otitis" Sixty-eighth Annual Session of the American Academy of Ophthalmology and Otolaryngology, Oct. 20-25, 1963, New York, NY, pp. 888-889.

Santa Barbara Medco, Inc. "Otological Ventilation Tubes" Product Brochure from http://www.sbmedco.com/ptfe_shepard.asp, 8 pages (Feb. 11, 2001).

Rhinology Products, Boston Medical Products, www.bosmed.com [date of publication unknown], pp. 1-16.

\* cited by examiner

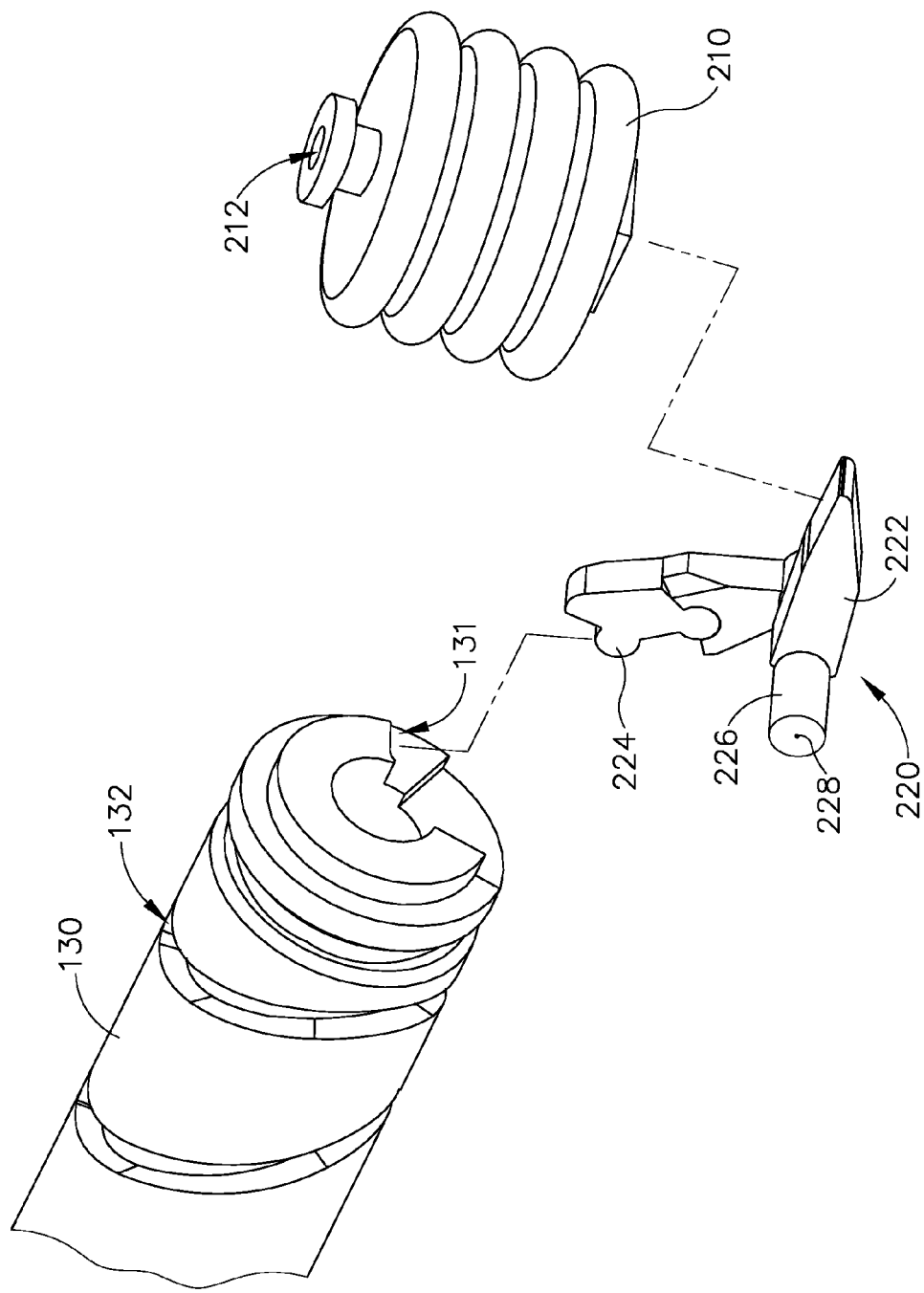

TYMPANOSTOMY TUBE DELIVERY DEVICE WITH CUTTING DILATOR

BACKGROUND

Some children may exhibit recurrent episodes of otitis media and/or -otitis media with effusion. Treatment of severe cases may involve the placement of a pressure equalization tube or tympanostomy tube through the tympanic membrane to provide adequate drainage of the middle ear by providing fluid communication between the middle and outer ear. In particular, such a tube may provide a vent path that promotes drainage of fluid from the middle ear via the Eustachian tube and may thus reduce stress imposed on the tympanic membrane from pressure within the middle ear. This may further reduce the likelihood of future infections and pressure induced ruptures of the tympanic membrane. Pressure equalization tubes may fall out spontaneously within about a year of placement. Exemplary pressure equalization tube delivery systems are disclosed in U.S. Pat. No. 8,052,693, entitled "System and Method for the Simultaneous Automated Bilateral Delivery of Pressure Equalization Tubes," issued Nov. 8, 2011, the disclosure of which is incorporated by reference herein. Additional exemplary pressure equalization tube delivery systems are disclosed in U.S. Pat. No. 8,249,700, entitled "System and Method for the Simultaneous Bilateral Integrated Tympanic Drug Delivery and Guided Treatment of Target Tissues within the Ears," issued Aug. 21, 2012, the disclosure of which is incorporated by reference herein. Still additional exemplary pressure equalization tube delivery systems are disclosed in U.S. Pub. No. 2011/0015645, entitled "Tympanic Membrane Pressure Equalization Tube Delivery System," published Jan. 20, 2011, the disclosure of which is incorporated by reference herein.

Insertion of a pressure equalization tube may be performed using general anesthesia in some cases, which may require additional resources such as an operating room, the presence of an anesthesiologist, and time in a recovery room. Furthermore, the use of general anesthesia may include certain risks that a patient may or may not be comfortable with undertaking. Some pressure equalization tube delivery systems and methods provide a local anesthetic through iontophoresis. Examples of such systems and methods are disclosed in U.S. Pub. No. 2010/0198135, entitled "Systems and Methods for Anesthetizing Ear Tissue," published Aug. 5, 2010, the disclosure of which is incorporated by reference herein. Additional examples of such systems and methods are disclosed in U.S. Pat. No. 8,192,420, entitled "Iontophoresis Methods," issued Jun. 5, 2012, the disclosure of which is incorporated by reference herein.

While a variety of pressure equalization tube delivery systems and methods have been made and used, it is believed that no one prior to the inventor(s) has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 10 depicts an exploded perspective view of a trip mechanism of the actuation features of FIG. 3;

Figure 1:
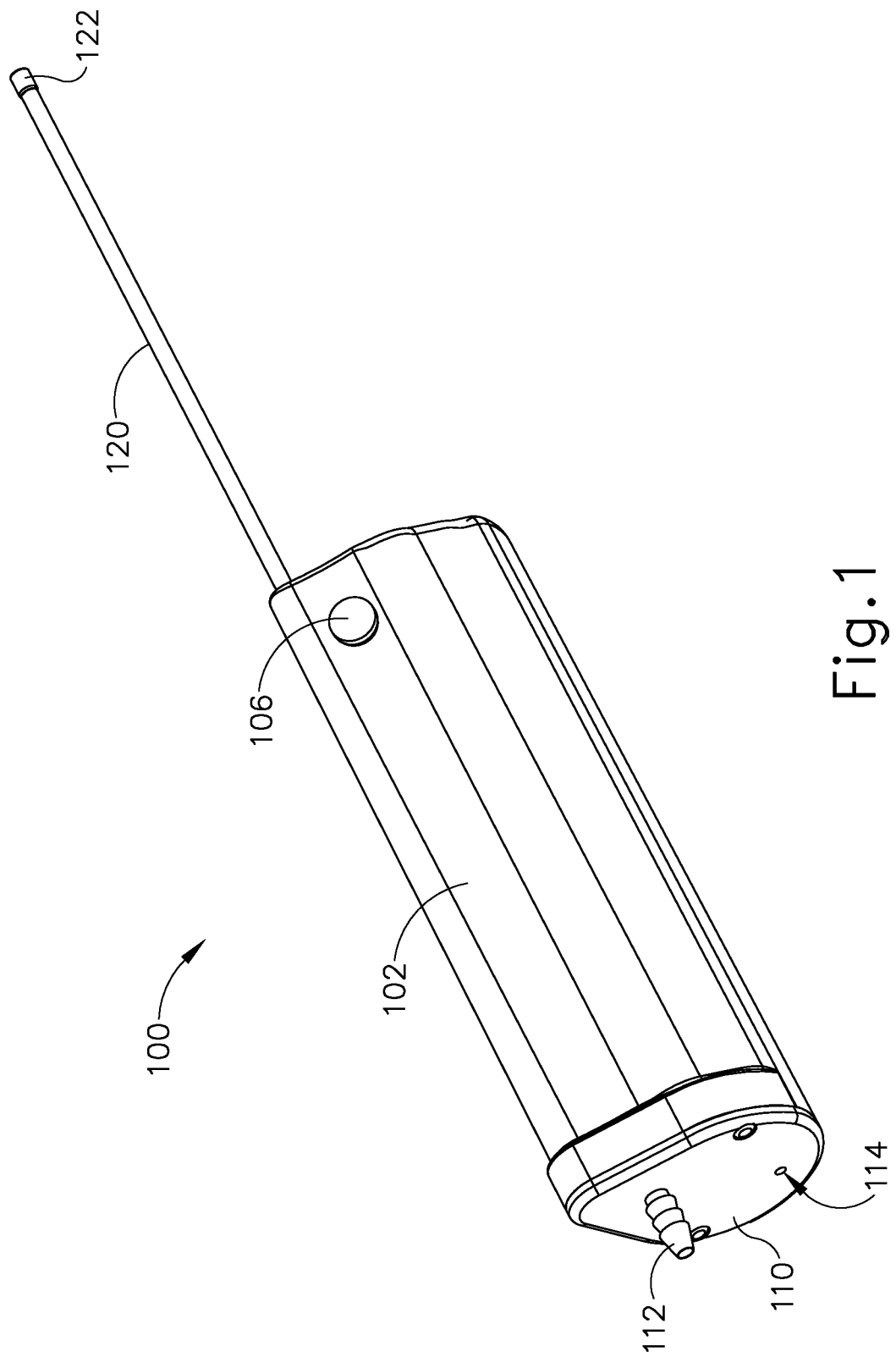
FIG. 1 depicts a perspective view of an exemplary pressure equalization tube delivery device (PETDD)

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Tympanic Tube Delivery Instrument

As noted above, a pressure equalization (PE) tube may be delivered to the tympanic membrane (TM) of a patient as a way of treating, for example, otitis media. In some instances, a delivery instrument may be used to insert PE tubes in the tympanic membrane (TM) without the use of general anesthesia. FIG. 1 shows an exemplary equalization tube delivery device (PETDD) (100) that may be used in such procedures. It should be understood that PETDD (100) may be used with an endoscope to provide visualization of the tympanic membrane (TM) during use of PETDD (100). It should also be understood that a patient may receive local anesthesia at the tympanic membrane (TM) through a process of iontophoresis before PETDD (100) is actuated to deploy a PE tube. By way of example only, such iontophoresis may be provided in accordance with at least some of the teachings of U.S. Pub. No. 2010/0198135, the disclosure of which is incorporated by reference herein; and/or in accordance with at least some of the teachings of U.S. Pat. No. 8,192,420, the disclosure of which is incorporated by reference herein. Other suitable ways in which PETDD (100) may be used will be apparent to those of ordinary skill in the art in view of the teachings herein.

As shown in FIG. 1, PETDD (100) of this example comprises a housing (102), a rear plate (110), and a cannula (120) extending distally from housing (102). Housing (102) is configured to be handheld, such that an operator may fully operate PETDD (100) using a single hand. Rear plate (110) includes a vacuum port (112) and a vent port (114). In the present example, vacuum port (112) is in the form of a barbed nib that is configured to couple with a conventional flexible tube; while vent port (114) is simply an opening formed through rear plate (110). Other suitable configurations for ports (112, 114) will be apparent to those of ordinary skill in the art in view of the teachings herein. Cannula (120) of the present example comprises an elongate tube having a clear tip (122) at the distal end of cannula (120). Clear tip (122) is configured to contact a patient's tympanic membrane (TM) while enabling visualization of the distal end of cannula (120). Other than vacuum port (112), rear plate (110) is hermetically sealed relative to housing (102). The interface between cannula (120) and housing (102) is also hermetically sealed. Thus, the interior of housing (102) defines a fluid tight hollow interior that is in fluid communication with vacuum port (112) and an interior region of cannula (120), where "fluid" in the context of this description includes compressible fluid such as air.

Figure 2:
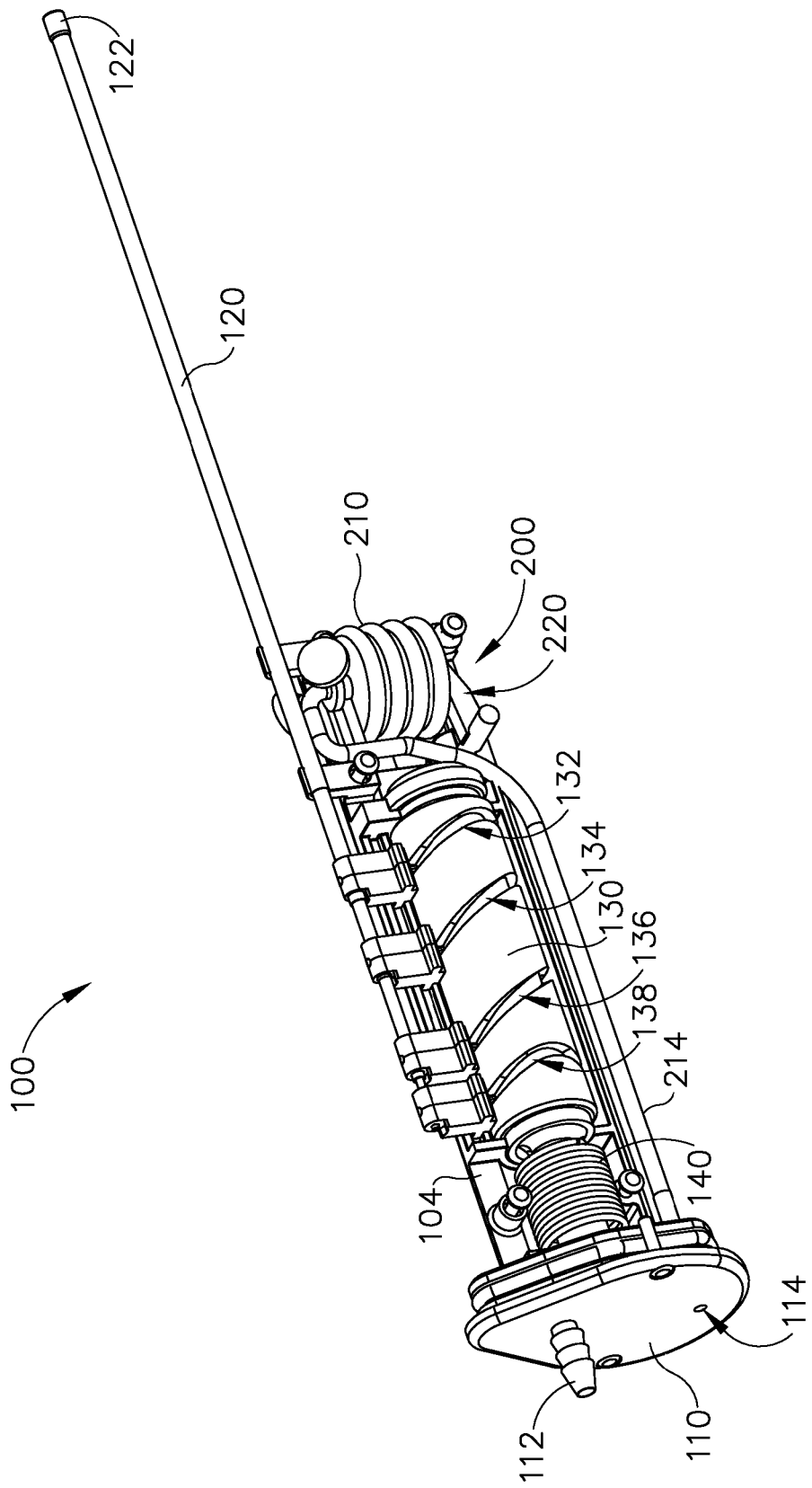
FIG. 2 depicts a perspective view of the PETDD of FIG. 1, with the housing omitted and a chassis half omitted.

As shown in FIG. 2, a chassis (104) is coupled with housing (102) and supports several components within housing (102). In the present example, a second chassis (not shown) is coupled with chassis (104) and is structurally substantially identical from chassis (104), but is omitted from FIG. 2 just to enable viewing of features that would otherwise be obscured by the second chassis. As can be seen in FIG. 2, chassis (104) supports a camshaft (130) and a trip mechanism (200). Camshaft (130) includes a dilator track (132), a shield tube track (134), a pusher track (136), and a piercer track (138). Tracks (132, 134, 136, 138) are formed as recesses in camshaft (130) and each track (132, 134, 136, 138) has a unique configuration in order to provide a particular sequence of operation of translating components as will be described in greater detail below. A torsion spring (140) is coupled to the proximal end of camshaft (130). Torsion spring (140) is also grounded against the distal face of rear plate (110). Torsion spring (140) resiliently provides a rotational bias to camshaft (130). In particular, torsion spring (140) urges camshaft (130) to rotate in the clockwise direction (viewed from the distal end of PETDD (100) toward the proximal end of PETDD (100)) about the longitudinal axis of camshaft (130). As will be described in greater detail below (200), trip mechanism selectively resists such rotation. While torsion spring (140) is used to bias camshaft (130) in the present example, it should be understood that any other suitable types of components may be used to bias camshaft (130).

Figure 3:
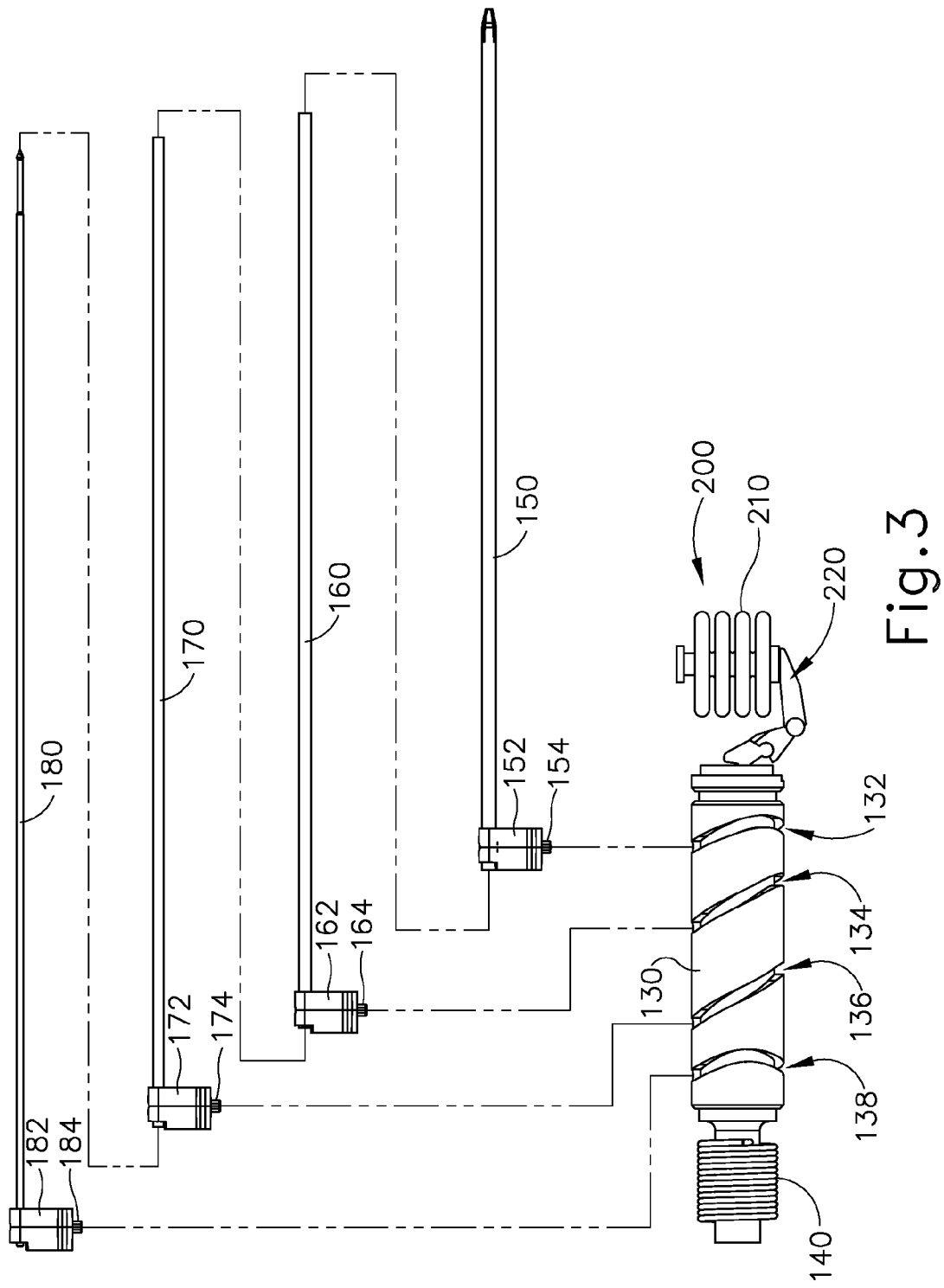
FIG. 3 depicts an exploded elevational view of actuation features of the PETDD of FIG. 1.

As shown in FIG. 3, various components are engaged with camshaft (130) and are thereby actuated by rotation of camshaft (130). In particular, a dilator tube (150), a shield tube (160), a pusher tube (170), and a piercer (180) are all engaged with camshaft (130). Tubes (150, 160, 170) and piercer (180) are all coaxially disposed within cannula (120). Piercer (180) is coaxially and slidably disposed within pusher tube (170), which is coaxially and slidably disposed within shield tube (160), which is coaxially and slidably disposed within dilator tube (150), which is coaxially and slidably disposed within cannula (120). Tubes (150, 160, 170) and piercer (180) all translate relative to cannula (120) in a particular sequence in order to deploy a PE tube as will be described in greater detail below. This sequence is driven by rotation of camshaft (130).

A cam follower (152) is fixedly secured to the proximal end of dilator tube (150). Cam follower (152) includes a laterally projecting pin (154) that is disposed in dilator track (132), such that rotation of camshaft (130) causes cam follower (152) and dilator tube (150) to translate. Similarly, a cam follower (162) is fixedly secured to the proximal end of shield tube (160). Cam follower (162) includes a laterally projecting pin (164) that is disposed in shield tube track (134), such that rotation of camshaft (130) causes cam follower (162) and shield tube (160) to translate. A cam follower (172) is fixedly secured to the proximal end of pusher tube (170). Cam follower (172) includes a laterally projecting pin (174) that is disposed in pusher tube track (136), such that rotation of camshaft (130) causes cam follower (172) and pusher tube (170) to translate. Finally, a cam follower (182) is fixedly secured to the proximal end of piercer (180). Cam follower (182) includes a laterally projecting pin (184) that is disposed in piercer track (138), such that rotation of camshaft (130) causes cam follower (182) and piercer (180) to translate.

Figure 4:
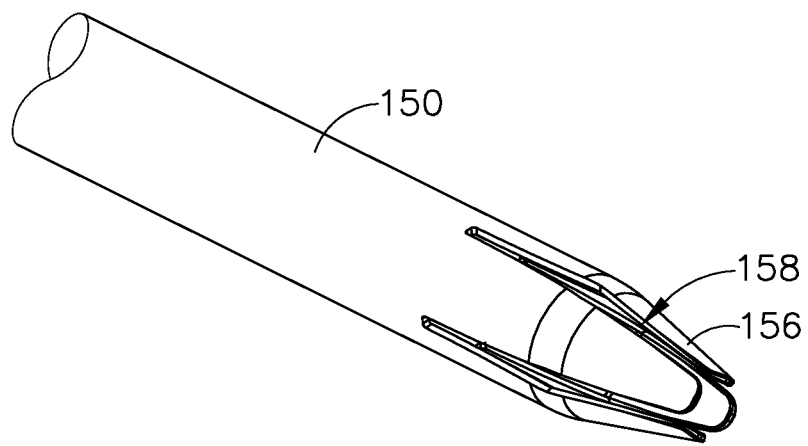
FIG. 4 depicts a perspective view of the distal end of a dilator of the actuation features of FIG. 3.
Figure 5:
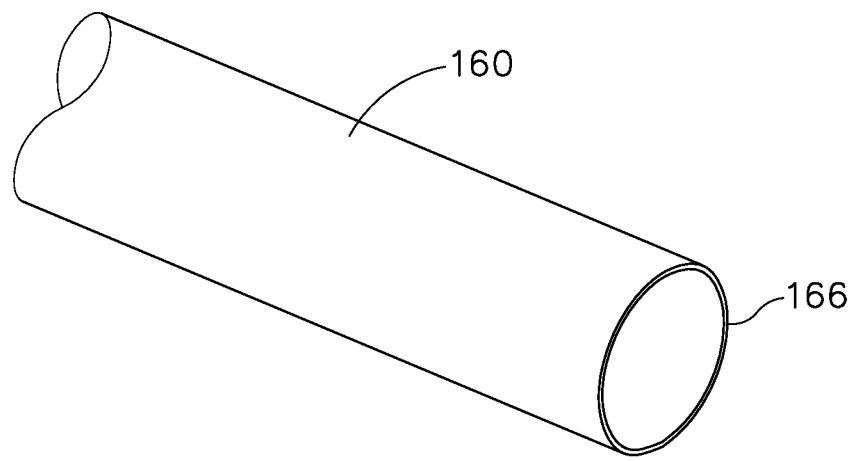
FIG. 5 depicts a perspective view of the distal end of a shield tube of the actuation features of FIG. 3.
Figure 6:
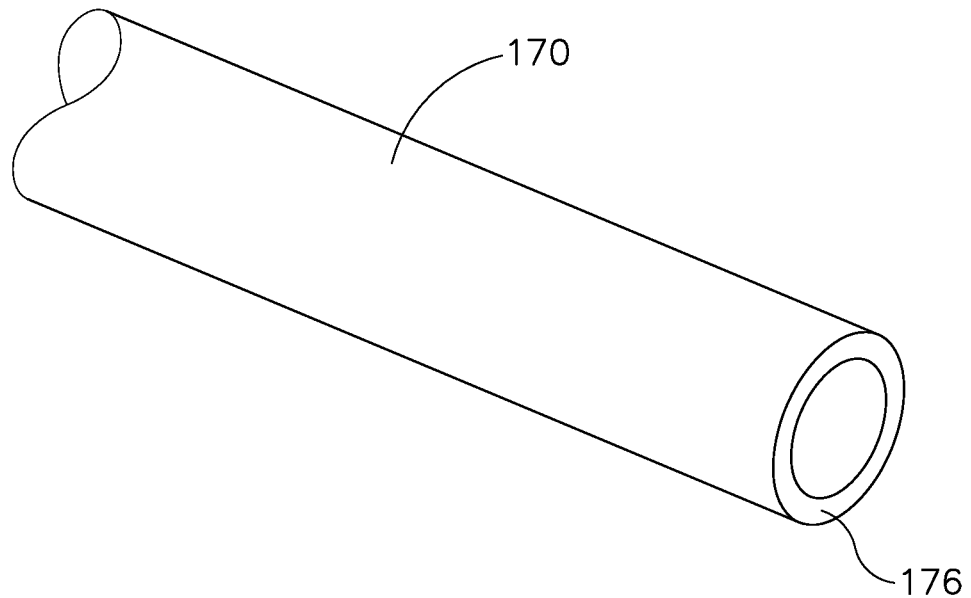
FIG. 6 depicts a perspective view of the distal end of a pusher of the actuation features of FIG. 3.
Figure 7:
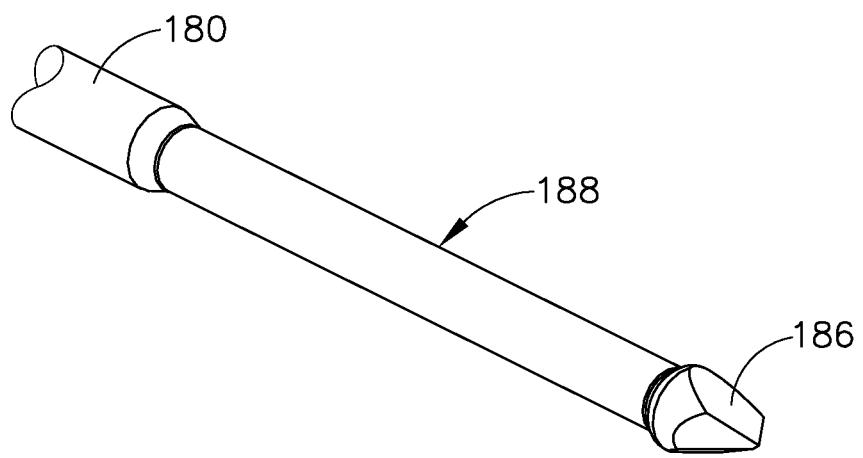
FIG. 7 depicts a perspective view of the distal end of a piercer of the actuation features of FIG. 3.

As shown in FIG. 4, the distal end of dilator tube (150) includes a plurality of generally flexible leaves (156) that are separated by longitudinally extending gaps (158). Leaves (156) are resiliently biased to assume the inwardly deflected positioning shown in FIG. 4; but are operable to flex outwardly from this positioning as will be described in greater detail below. As shown in FIG. 5, the distal end of shield tube (160) simply includes a circular edge (166). As shown in FIG. 6, the distal end of pusher tube (170) includes a distal face (176). In the present example, the difference between the inner diameter of pusher tube (170) and the outer diameter of pusher tube (170) is greater than the difference between the inner diameter of shield tube (160) and the outer diameter of shield tube (160). Thus, distal face (176) presents a more prominent contact surface than circular edge (166). As shown in FIG. 7, the distal end of piercer (180) includes a sharp, multi-faceted tip (186) that is configured to pierce through a patient's tympanic membrane (TM). In the present example, piercer (180) also includes a neck-down region (188) having a reduced diameter.

Figure 8:
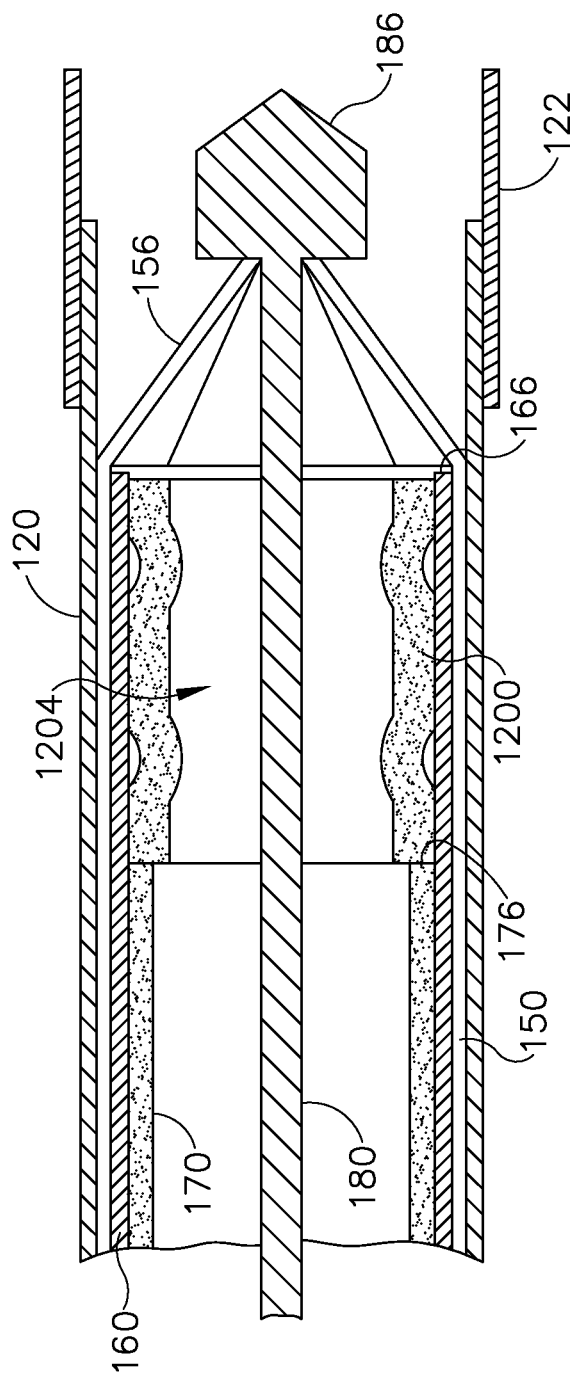
FIG. 8 depicts a cross-sectional side view of the actuation features of FIG. 3 with an exemplary pressure equalization (PE) tube.
Figure 13:
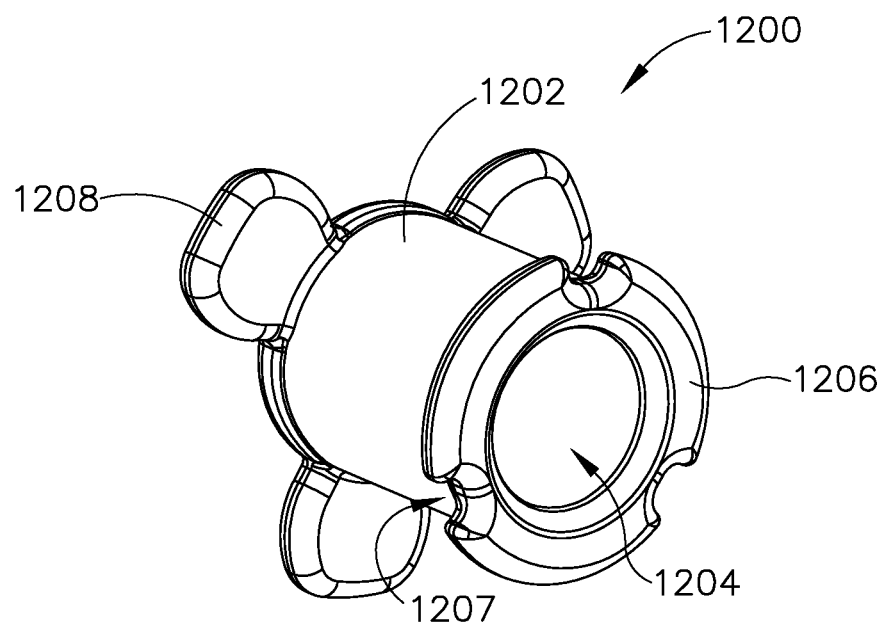
FIG. 13 depicts a perspective view of the proximal side of an exemplary PE tube suitable for delivery by the PETDD of FIG. 1.
Figure 14:
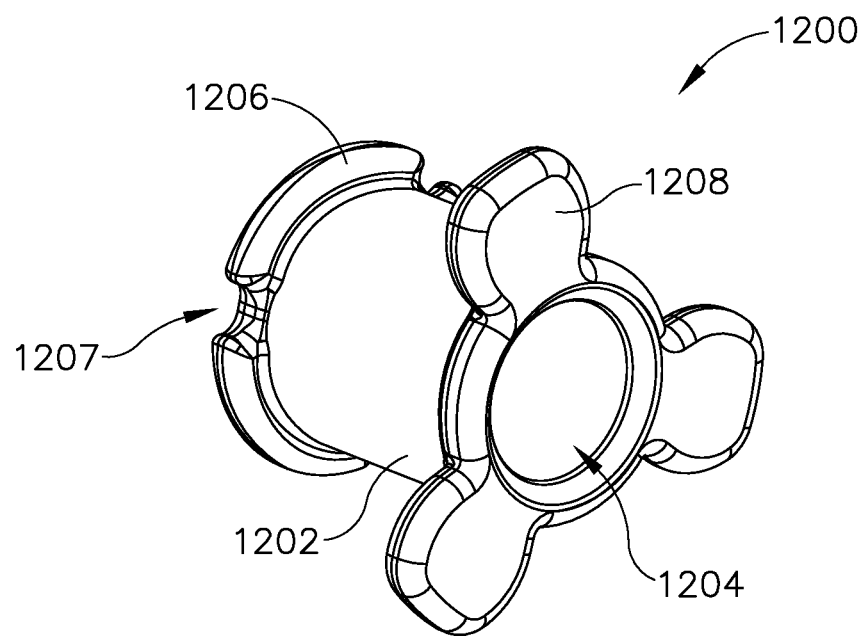
FIG. 14 depicts a perspective view of the distal side of the PE tube of FIG. 13.
Figure 15:
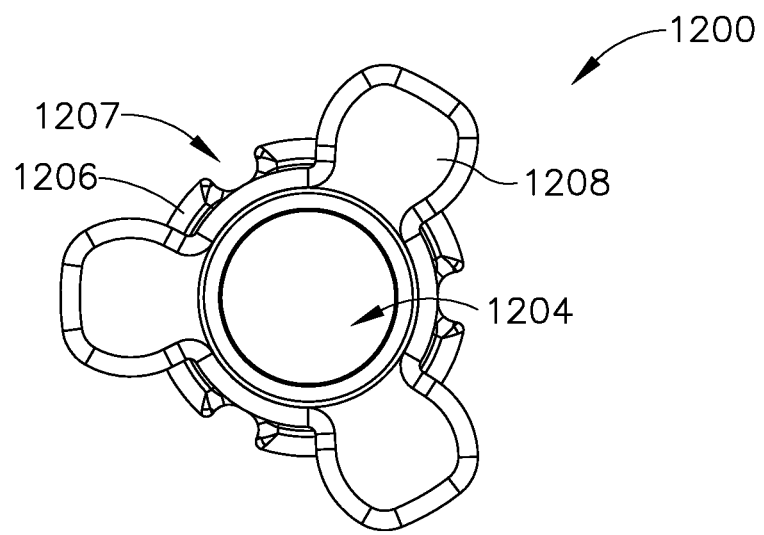
FIG. 15 depicts a distal elevational view of the PE tube of FIG. 13.
Figure 16:
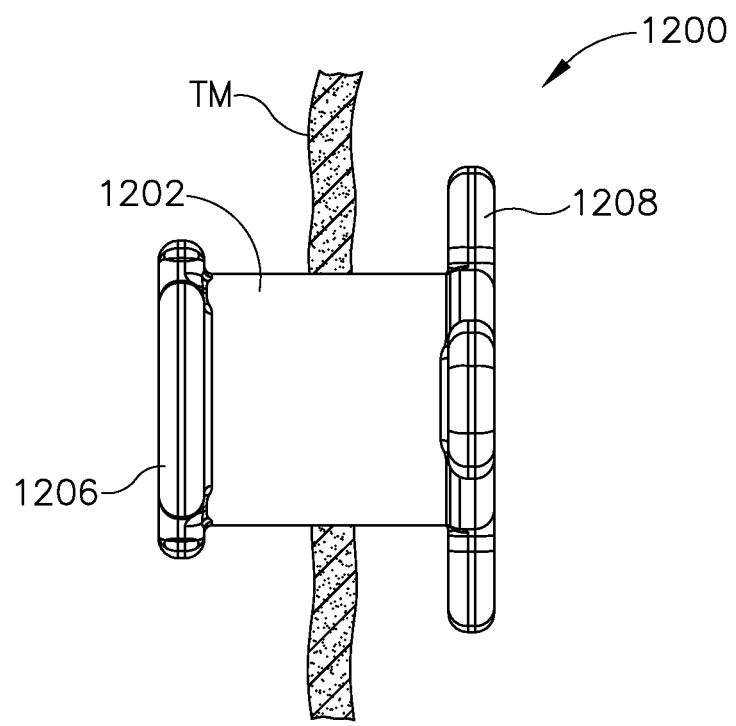
FIG. 16 depicts a side elevational view of the PE tube of FIG. 13, positioned within a tympanic membrane.

FIG. 8 shows the positioning of tubes (150, 160, 170), piercer (180), and PE tube (1200) within cannula (120) before camshaft (130) starts rotating from a home position. As shown, tip (186) of piercer (180) is positioned distal to leaves (156) of dilator tube (150), such that leaves (156) are positioned about neck-down region (188) of piercer (180). PE tube (1200) is positioned within the distal end of shield tube (160), whose distal edge (166) is just proximal to leaves (156). Pusher tube (170) is proximal to PE tube (1200), with distal face (176) of pusher tube (170) abutting the proximal end of PE tube (1200). In the present example, PE tube (1200) is resiliently biased to assume a rivet-like shape presenting a distal flange (1208) and a proximal flange (1206) (see FIG. 13). However, PE tube (1200) is compressed against this bias, thereby assuming a generally cylindraceous configuration, when PE tube (1200) is disposed within shield tube (160) as shown in FIG. 8.

Figure 9:
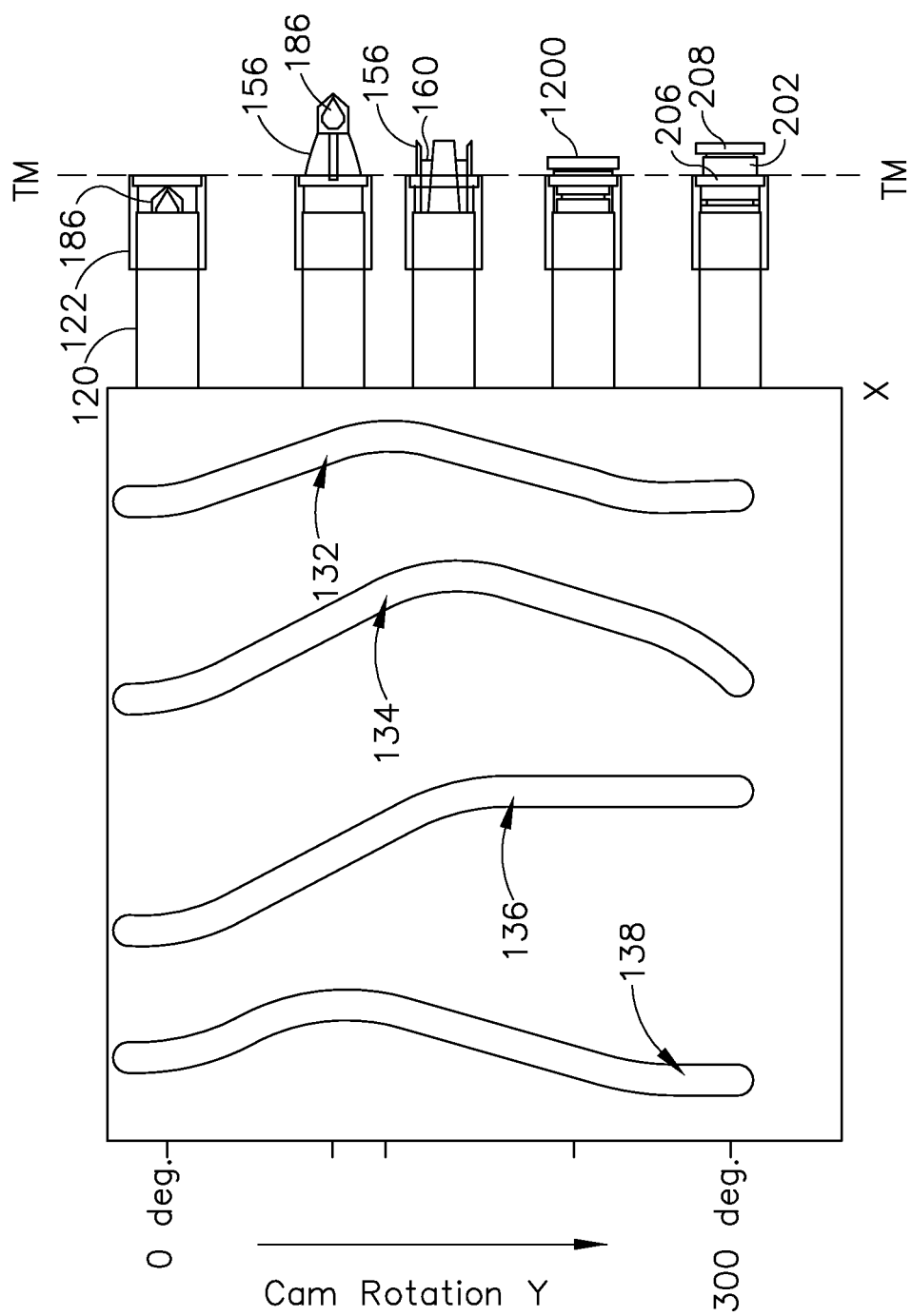
FIG. 9 depicts a displacement and operational diagram associated with the actuation features of FIG. 3.

FIG. 9 depicts a sequence of operation that occurs upon rotation of camshaft (130) from a home position to an actuated position, where tracks (132, 134, 136, 138) are shown developed into a flat pattern for purpose of illustration. The sequence starts at the top region of FIG. 9, which shows the distal end of clear tip (122) contacting the patient's tympanic membrane (TM). At this stage, tubes (150, 160, 170), piercer (180), and PE tube (1200) are at the positions shown in FIG. 8. Once camshaft (130) starts rotating at the urging of torsion spring (140), pins (154, 164, 174, 184) begin to ride along their respective tracks (132, 134, 136, 138), such that piercer tip (186) and leaves (156) are driven distally through the tympanic membrane (TM). While not directly shown in FIG. 8, it should be understood that tubes (160, 170, 190) are also driven distally during this transition, though tubes (160, 170, 190) remain proximal to clear tip (122) at this stage. As camshaft (130) continues to rotate, piercer (180) begins retracting proximally while tubes (160, 170, 190) continue to advance distally. As shown, shield tube (160) spreads leaves (156) outwardly from their default positions. This further dilates the puncture site in the tympanic membrane (TM). Shield tube (160) continues to contain PE tube (1200) at this stage. As camshaft (130) continues to rotate, piercer (180) and dilator (150) retract proximally behind clear tip (122). Shield tube (160) also begins to retract proximally, while pusher tube (170) remains longitudinally stationary. This relative movement uncovers the distal end of PE tube (1200), such that the resilient bias of PE tube (1200) is allowed to form distal flange (192) on the far side of the tympanic membrane (TM). Piercer (180) eventually returns to the fully proximal position, dilator (170) eventually returns to the fully proximal position, and pusher tube (170) eventually reaches a fully distal position. As camshaft (130) continues to rotate, shield tube (160) continues to retract proximally while pusher tube (170) remains longitudinally stationary. This relative movement uncovers the proximal end of PE tube (1200), such that the resilient bias of PE tube (1200) is allowed to form proximal flange (194) on the near side of the tympanic membrane (TM).

Upon completion of the above described sequence shown in FIG. 9, cannula (120) is withdrawn from the patient's ear, leaving the actuated PE tube (1200) in place in the patient's the tympanic membrane (TM). Flanges (192, 194) maintain the position of PE tube (1200) in TM, while the passageway formed by the interior (196) of PE tube (1200) (see FIG. 8) provides a path for fluid communication between the patient's inner ear and outer ear. This fluid path further provides pressure equalization between the patient's inner ear and outer ear.

As noted above, PETDD (100) of the present example includes a vacuum port (112) that is operable to couple with a vacuum source (not shown). As also noted above, this vacuum port (112) is in fluid communication with the interior of housing (102), which is further in fluid communication with cannula (120). It should be understood that cannula (120) and/or one of the tubes (150, 160, 170) within cannula (120) may provide a path for fluid communication between the interior of housing (102) and tip (122). By way of example only, such a path may be formed by a gap between the outer diameter of dilator tube (150) and the inner diameter of cannula (120). In addition or in the alternative, such a path may be formed through the interior of pusher tube (170), through interior (196) of PE tube (1200), and through gaps (158) between leaves (156) of dilator (150). Other suitable ways for providing a path for fluid communication between the interior of housing (102) and tip (122) will be apparent to those of ordinary skill in the art in view of the teachings herein. Regardless of how the path is formed, it should be understood that the path may be used to communicate a vacuum to tip (122), which may assist in drawing the tympanic membrane (TM) toward tip (122). For instance, an operator may make an initial contact between tip (122) and TM, then activate a vacuum source that is in communication with port (112) to communicate a vacuum to tip (122), thereby completing full contact between tip (122) and the tympanic membrane (TM). Such vacuum assisted contact may reduce risks that may be associated with operator error when the operator fails to achieve sufficient contact between tip (122) and the tympanic membrane (TM).

Figure 11A:
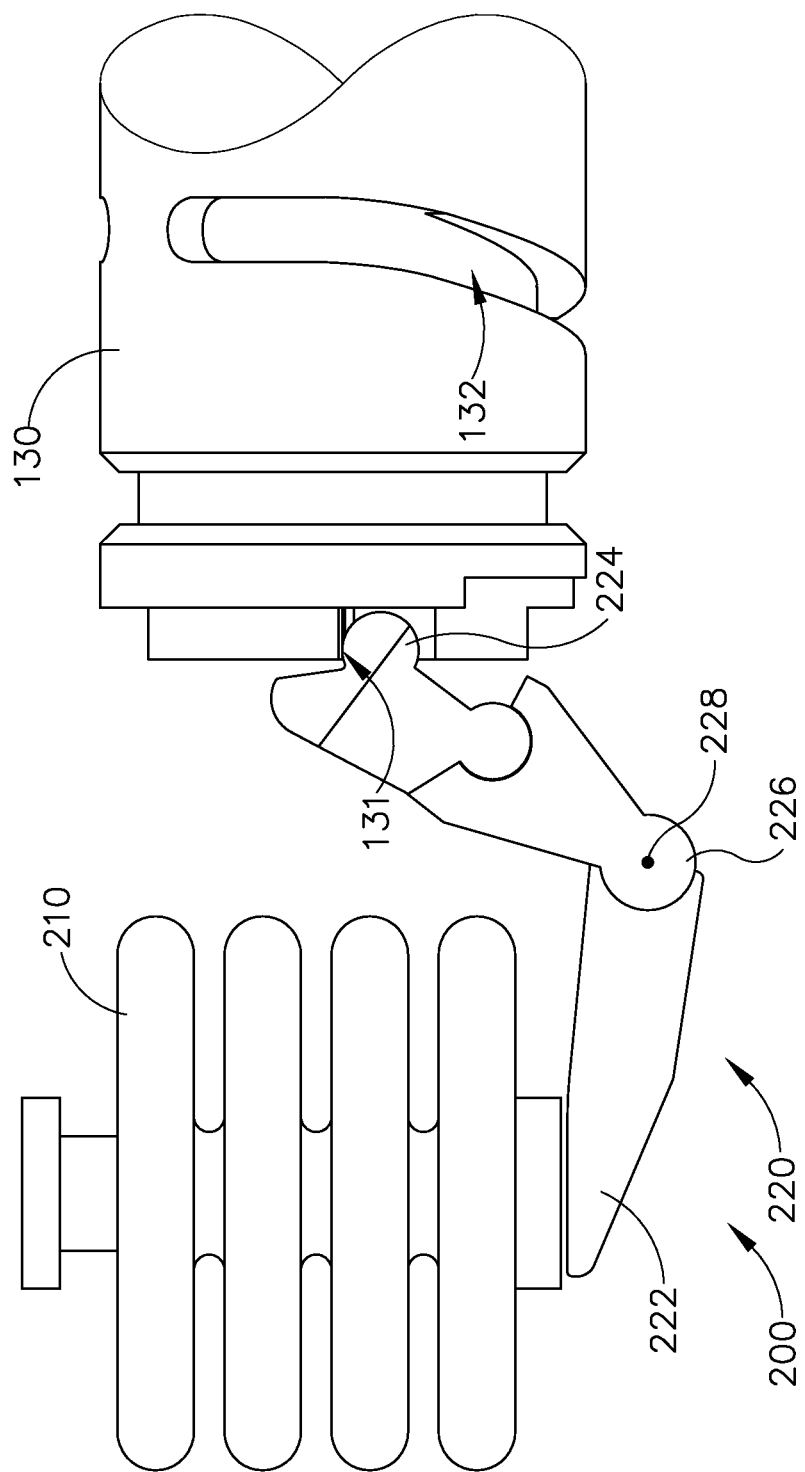
FIG. 11A depicts a side elevational view of the trip mechanism of FIG. 10, with a lever engaging a camshaft.
Figure 11B:
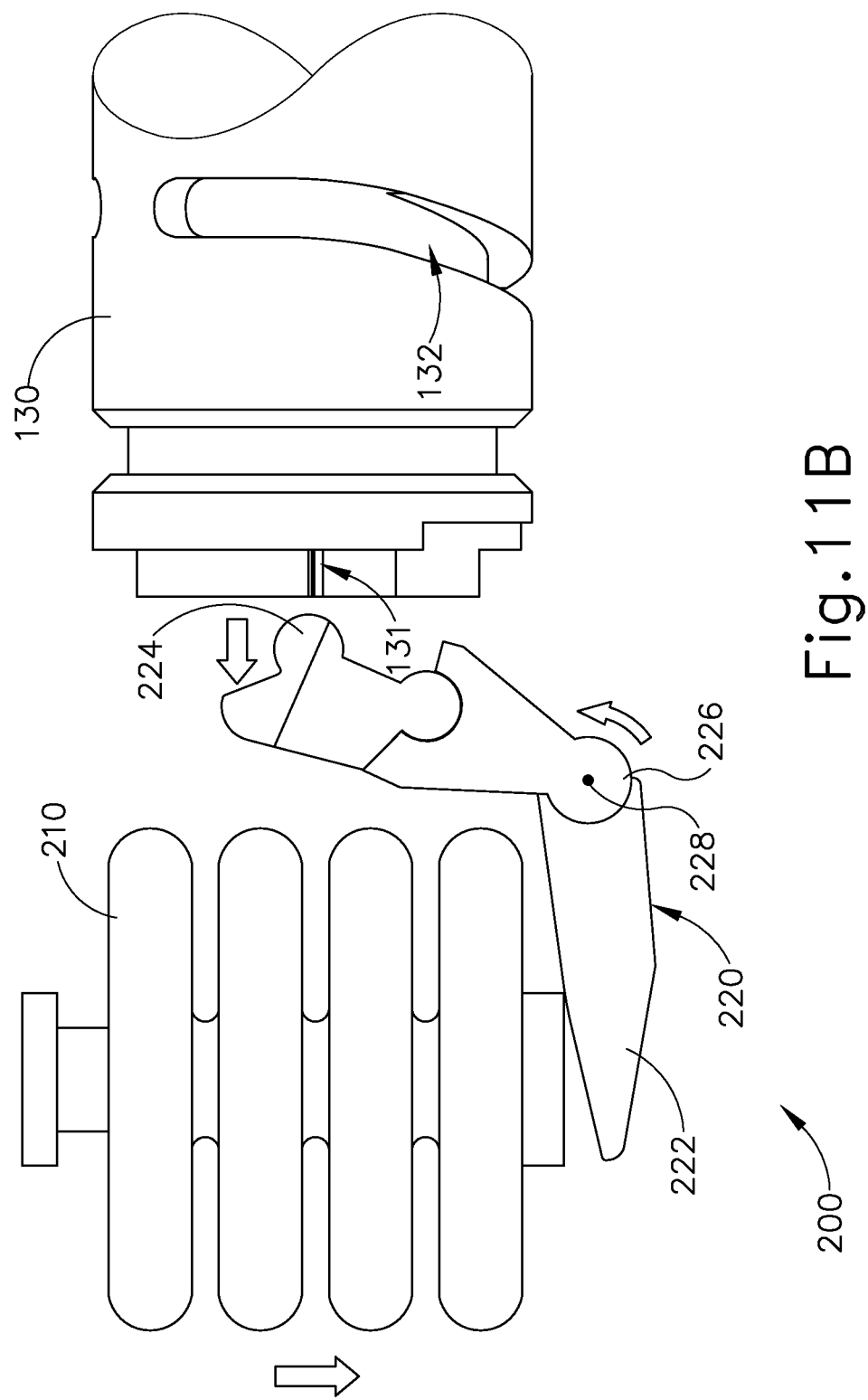
FIG. 11B depicts a side elevational view of the trip mechanism of FIG. 10, with the lever disengaged from the camshaft.

As also noted above, PETDD (100) of the present example includes a trip mechanism (200) that is configured to selectively resist rotation of camshaft (130) by torsion spring (140). As best seen in FIGS. 10-11, trip mechanism (200) of this example comprises an expandable bellows (210) and a pivoting member (220). Bellows (210) includes a fluid port (212) that is coupled with vent port (114) of rear plate (110) via a vent tube (214) (see FIG. 2). Bellows (210) is expandable from a compressed configuration (FIG. 11A)

to an expanded configuration (FIG. 11B). Pivoting member (220) includes a lever arm (222), a catch arm (224), and a pivot pin (226). Pivot pin (226) is pivotally supported by chassis (104) and defines a pivot axis (228). Lever arm (222) is positioned underneath bellows (210). Catch arm (224) is configured to selectively engage a catch feature (131) of camshaft (130). In particular, when pivoting member (220) is in a first position as shown in FIG. 11A, catch arm (224) is engaged with catch feature (131) of camshaft (130). This engagement presents camshaft (130) from rotating under the influence of torsion spring (140). When pivoting member (220) is in a second position as shown in FIG. 11B, catch arm (224) is disengaged from catch feature (131) of camshaft (130), enabling camshaft (130) to rotate under the influence of torsion spring (140) to provide the sequence of operation described above.

Trip mechanism (200) of the present example automatically transitions from a first position (FIG. 11A) to a second position (FIG. 11B) when a certain level of vacuum is achieved within the interior of housing (102). During an exemplary use of PETDD (100), tip (122) is positioned adjacent to a patient's tympanic membrane (TM) and then a vacuum source communicates a vacuum to tip (122) via port (112), the interior of housing (102), and components between housing (102) and tip (122). Before tip (122) reaches full contact with TM, the pressure within the interior of housing (102) may reduce slightly. However, once tip (122) reaches full contact with the tympanic membrane (TM) (e.g., due to suction drawing the tympanic membrane (TM) against tip (122)), the pressure within the interior of housing (102) will drop significantly. This pressure drop will be encountered by the exterior of bellows (210), while the interior of bellows (210) remains in fluid communication with atmospheric air via port (114). Bellows (210) will thus experience a pressure differential that will cause bellows (210) to expand from the position shown in FIG. 11A to the position shown in FIG. 11B.

It should be understood from the foregoing that a vacuum may be used to assist in achieving full apposition between tip (122) of cannula (120) and TM; and that once such apposition is achieved, trip mechanism (200) may effectively unlock camshaft (130) to thereby automatically trigger a PE tube (1200) deployment sequence.

In some versions, housing (102) also includes one or more lateral vent ports (106) that are positioned to be selectively covered or otherwise closed by the hand of the operator that is grasping housing (102). While FIG. 1 shows a single vent port (106), it should be understood that one or more additional vent ports (106) may be provided. In versions having a user actuated vent port (106), vent port (106) may act as a manual switch, providing an additional means for the operator to control actuation of PETDD (100). In particular, when a vacuum is communicated to vacuum port (112), such a vacuum may be essentially ineffective until the operator manually covers or otherwise closes vent port (106). The vacuum may simply draw atmospheric air into an open vent port (106). Once the operator covers or otherwise closes vent port (106), the vacuum within housing (102) may provide the full apposition of the tympanic membrane (TM) against tip (122) and may provide the pressure differential that expands bellows (210) for actuation of trip mechanism (200). Regardless of whether a vent port (106) is provided, it should be understood that a hand switch, foot switch, and/or other type of user input may be interposed between a vacuum source and vacuum port (112) to provide the operator with further control of vacuum. It should also be understood that simply placing a finger over vent port (106) to close vent port (106) may impose less lateral force on PETDD (100) than pushing an activation button laterally on PETDD (100) might impose. Thus, vent port (106) may provide a greater stability and a reduced risk of inadvertent repositioning of PETDD (100) through operator error at the time of actuation.

Figure 12:
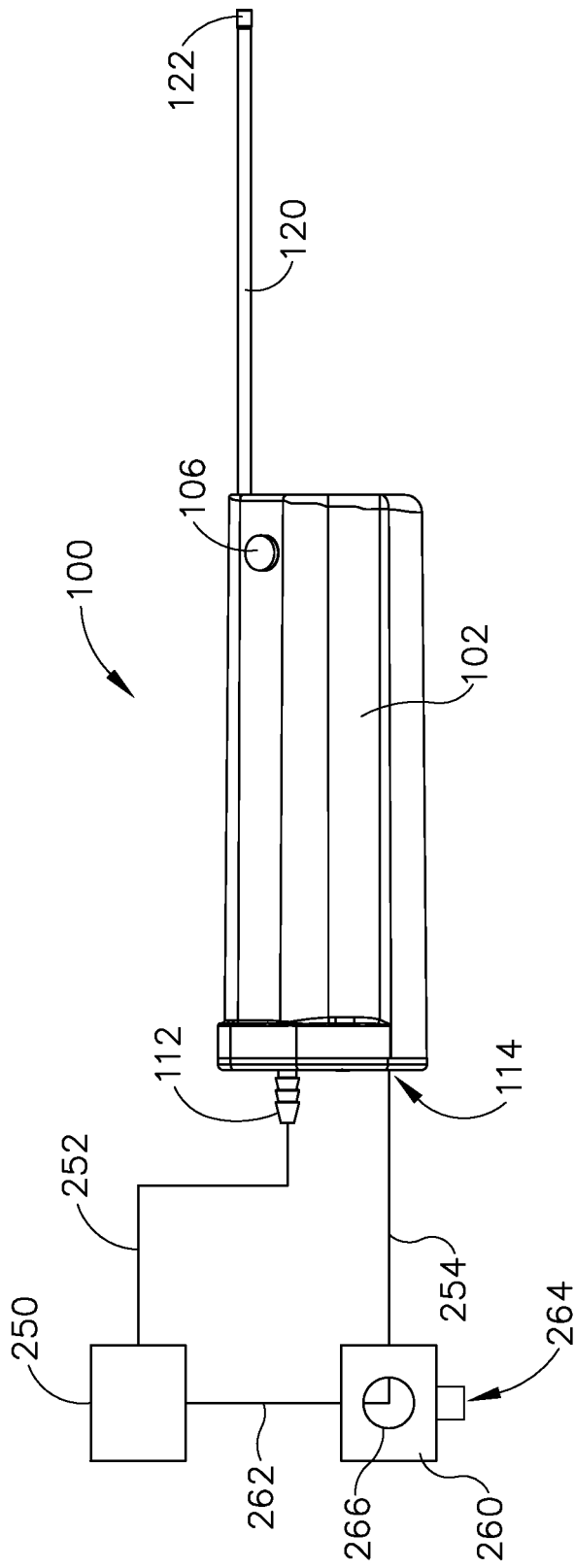
FIG. 12 depicts a side diagrammatic view of an exemplary alternative system incorporating the PETDD of FIG. 1.

FIG. 12 shows a merely exemplary alternative pneumatic configuration for PETDD (100). In this example, vacuum port (112) is directly coupled with a vacuum source (250) via a conduit (252). Vent port (114) is directly coupled with a valve assembly (260) via a conduit (254). Valve assembly (260) provides one fluid path leading to vacuum source (250) via a conduit (262); and another fluid path leading to a vent port (264). A valve (266) within valve assembly (260) selectively couples conduit (254) with either conduit (262) or vent port (264). In an exemplary use of this system, valve (266) may initially couple conduit (254) with conduit (262), such that the interior of housing (102) and the interior of bellows (210) receive the same vacuum simultaneously. In this example, bellows (210) remains compressed even when tip (122) achieves full apposition with the tympanic membrane (TM) since bellows (210) is not experiencing a pressure differential when valve (266) is positioned to couple conduit (254) with conduit (262). Once the operator is ready to actuate PETDD (100), the user may switch valve (266) to couple conduit (254) with port (114), thereby coupling the interior of bellows (210) with atmospheric air. Since the interior of housing (102) continues to receive a vacuum, this switching of valve (266) provides the pressure differential for expansion of bellows (210), which releases camshaft (130) for rotation as described above. Other suitable arrangements and pneumatic schemes will be apparent to those of ordinary skill in the art in view of the teachings herein.

II. Exemplary Pressure Equalization Tube

FIGS. 13-16 show PE tube (1200) in greater detail. PE tube (1200) of this example includes a cylindraceous body (1202) that defines a passageway (1204). A flange (1206) is located at the proximal end of body (1202) while a set of petals (1208) are located at the distal end of body (1202). Flange (1206) includes a plurality of inwardly directed recesses (1207). Recesses (1207) are configured to facilitate flexing of flange (1206) from an outwardly extended position to a generally cylindraceous position where the material forming flange (1206) extends longitudinally. While three recesses (1207) are shown, it should be understood that any other suitable number of recesses (1207) may be provided. Similarly, while three petals (1208) are shown, it should be understood that any other suitable number of petals (1208) may be provided.

PE tube (1200) is formed of a resilient material that is biased to assume the rivet like configuration shown in FIGS. 13-16. However, flange (1206) and petals (1208) may be flexed inwardly toward the longitudinal axis of body (1202) to provide PE tube (1200) with a cylindraceous configuration. In particular, flange (1206) and petals (1208) may be flexed such that their outer surfaces are at the same radial distance from the longitudinal axis as the outer perimeter of body (1202). This radial distance may be slightly less than the radial distance associated with the inner diameter of shield tube (160), such that PE tube (1200) may collapse to fit within shield tube (160). When PE tube (1200) is disposed in a tympanic membrane (TM), petals (1208) are located medially (i.e., on the middle ear side) while flange (1206) is located laterally (i.e., on the outer ear side). By way of example only, PE tube (1200) may also be configured in accordance with at least some of the teachings of U.S. patent application Ser. No. 13/800,113, entitled "Tympanic Membrane Pressure Equalization Tube," filed on Mar. 13, 2013, the disclosure of which is incorporated by reference herein; and/or at least some of the teachings of U.S. patent application Ser. No. 13/804,553, entitled "Features to Improve and Sense Tympanic Membrane Apposition by Tympanostomy Tube Delivery Instrument," filed on Mar. 14, 2013, the disclosure of which is incorporated by reference herein. Other suitable forms that PE tube (1200) may take will be apparent to those of ordinary skill in the art in view of the teachings herein.

III. Exemplary Dilator with Integral Cutting Features

In some instances, it may be desirable to consolidate the functionality of dilator tube (150) and piercer (180) in a single structure. In other words, it may be desirable to provide a component within cannula (120) that is operable to both create a myringotomy incision in the tympanic membrane (TM) like piercer (180) and expand the myringotomy incision like dilator tube (150). Such a component may be expandable in response to distal advancement of shield tube (160), similar to dilator tube (150). Such a component may also be driven by a cam follower like cam follower (152). The following examples represent merely illustrative variations of dilator tube (150) that are operable to both create a myringotomy incision in the tympanic membrane (TM) like piercer (180) and expand the myringotomy incision like dilator tube (150).

While the examples are provided herein in the context of PETDD (100), it should be understood that the variations of dilator tube (150) discussed below may also be readily incorporated into a variety of other PETDDs. By way of example only, the variations of dilator tube (150) discussed below may be readily incorporated in any of the PETDDs disclosed in U.S. Pub. No. 2010/0198135, the disclosure of which is incorporated by reference herein. As another merely illustrative example, the variations of dilator tube (150) discussed below may be readily incorporated into any of the PETDDs disclosed in U.S. patent application Ser. No. 13/800,113, entitled "Tympanic Membrane Pressure Equalization Tube," filed on Mar. 13, 2013, the disclosure of which is incorporated by reference herein; and/or U.S. Pat. No. 9,320,652, entitled "Features to Improve and Sense Tympanic Membrane Apposition by Tympanostomy Tube Delivery Instrument," issued on Apr. 26, 2016, the disclosure of which is incorporated by reference herein. Still other PETDD variations that may incorporate the variations of dilator tube (150) discussed below will be apparent to those of ordinary skill in the art in view of the teachings herein.

A. Exemplary Dilator with Sharp Distal Point

Figure 17:
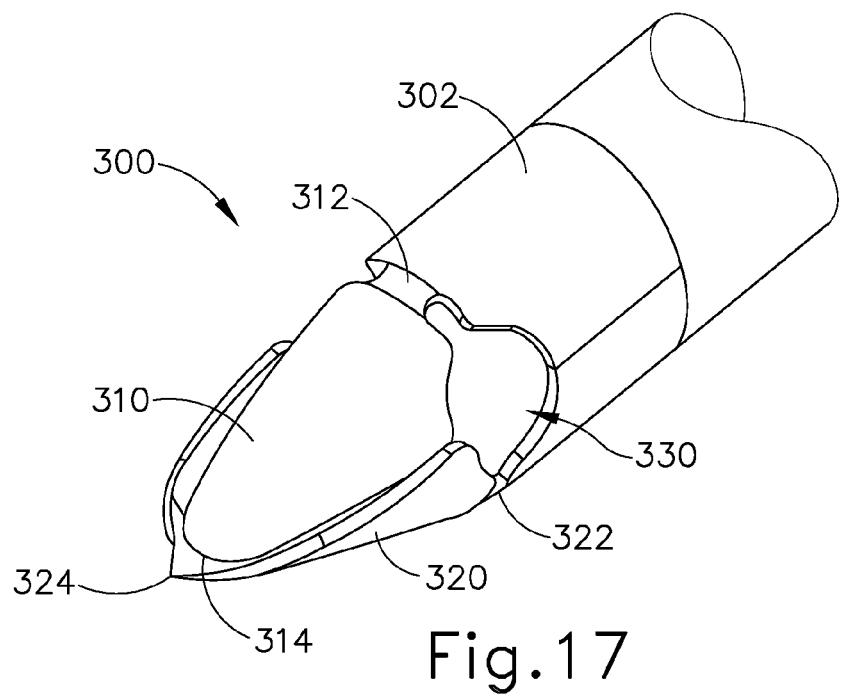
FIG. 17 depicts a perspective view of the distal end of an exemplary alternative dilator tube that may be readily incorporated in the PETDD of FIG. 1, in a collapsed state.
Figure 18:
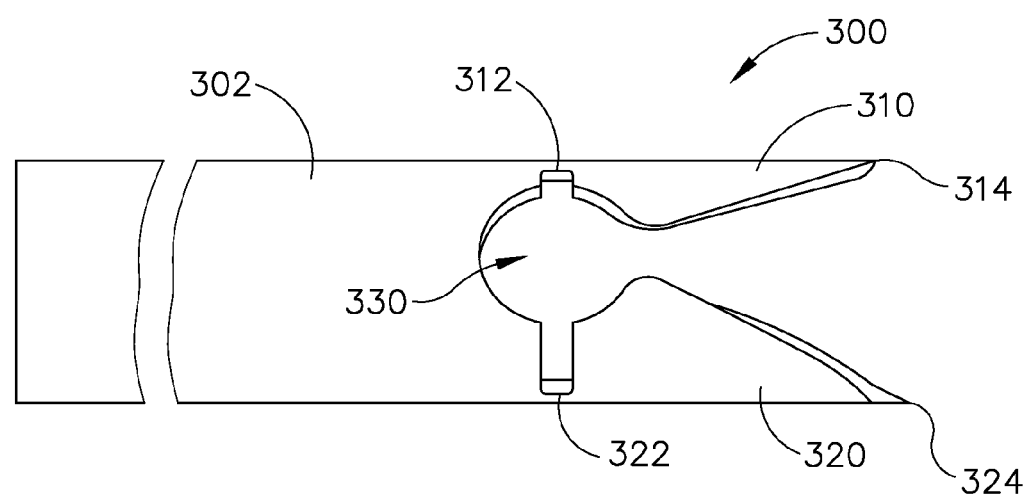
FIG. 18 depicts a side elevational view of the dilator tube of FIG. 17, in an expanded state.
Figure 19:
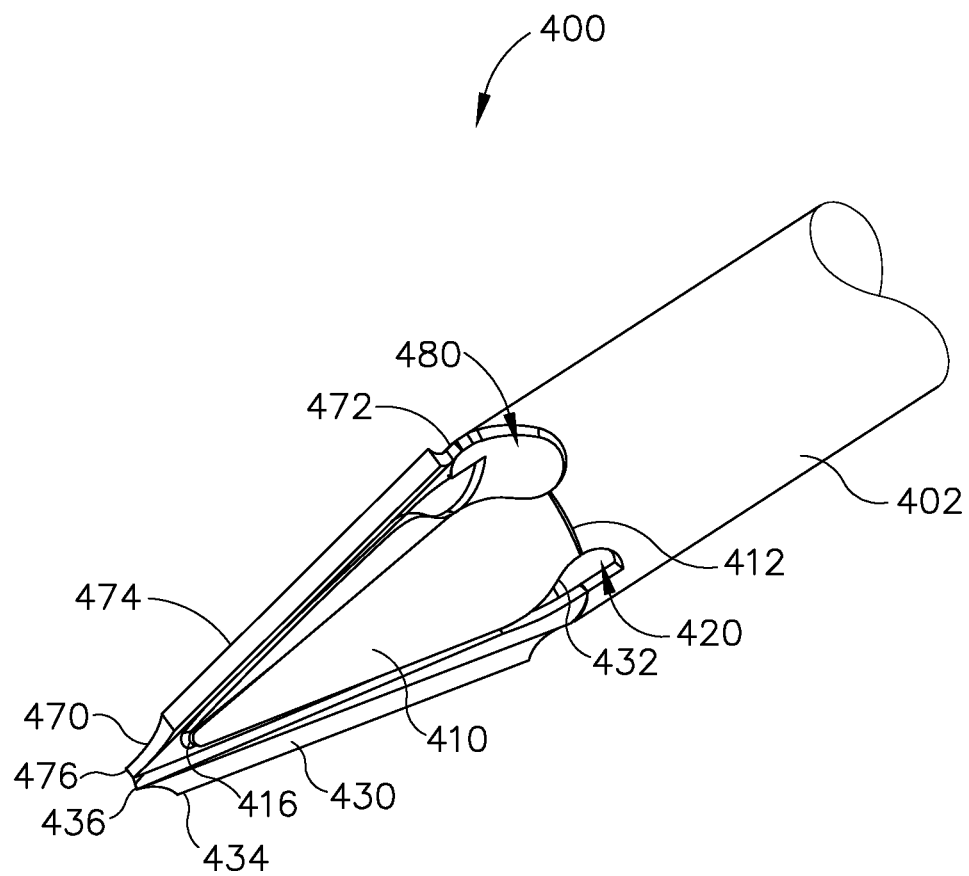
FIG. 19 depicts a perspective view of the distal end of another exemplary alternative dilator tube that may be readily incorporated in the PETDD of FIG. 1, in a collapsed state.
Figure 20:
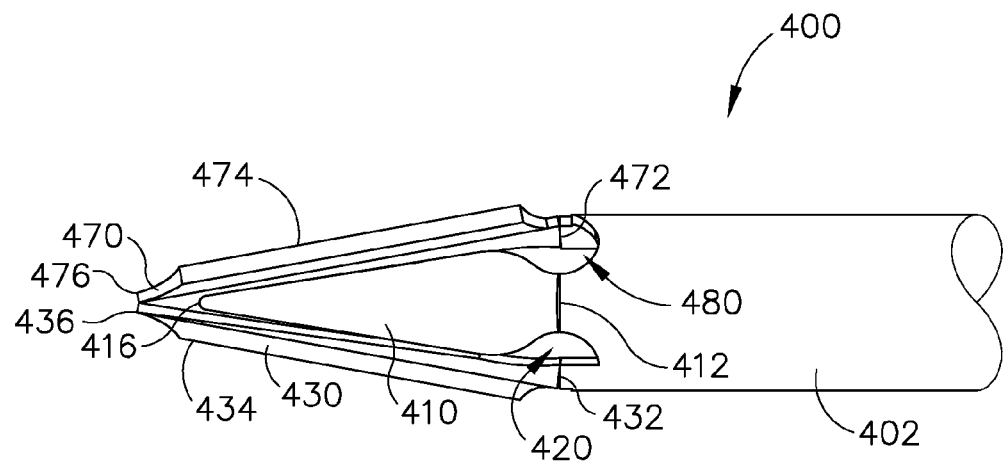
FIG. 20 depicts a side elevational view of the dilator tube of FIG. 19, in the collapsed state.
Figure 21:
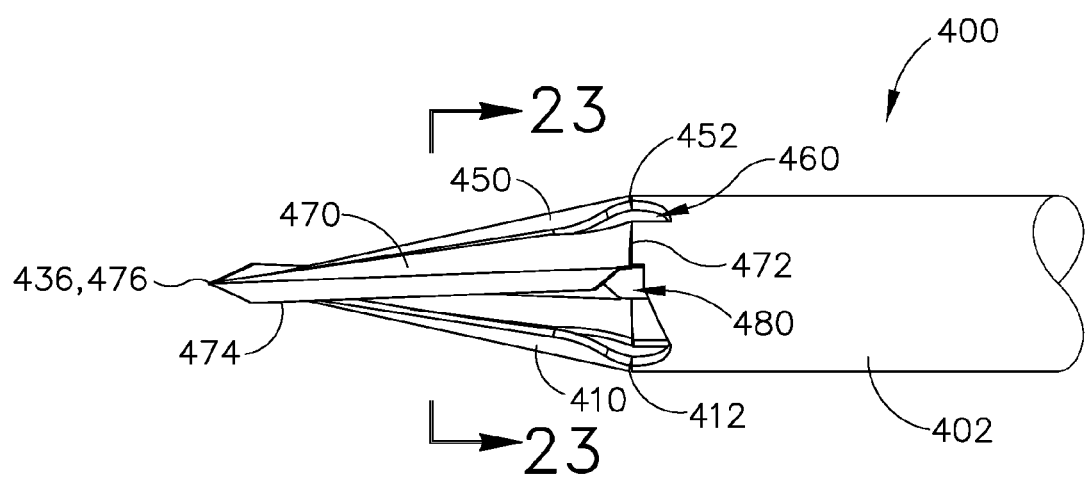
FIG. 21 depicts another side elevational view of the dilator tube of FIG. 19, in the collapsed state, rotated 90 degrees about the longitudinal axis of the dilator tube from the position shown in FIG. 20.
Figure 22:
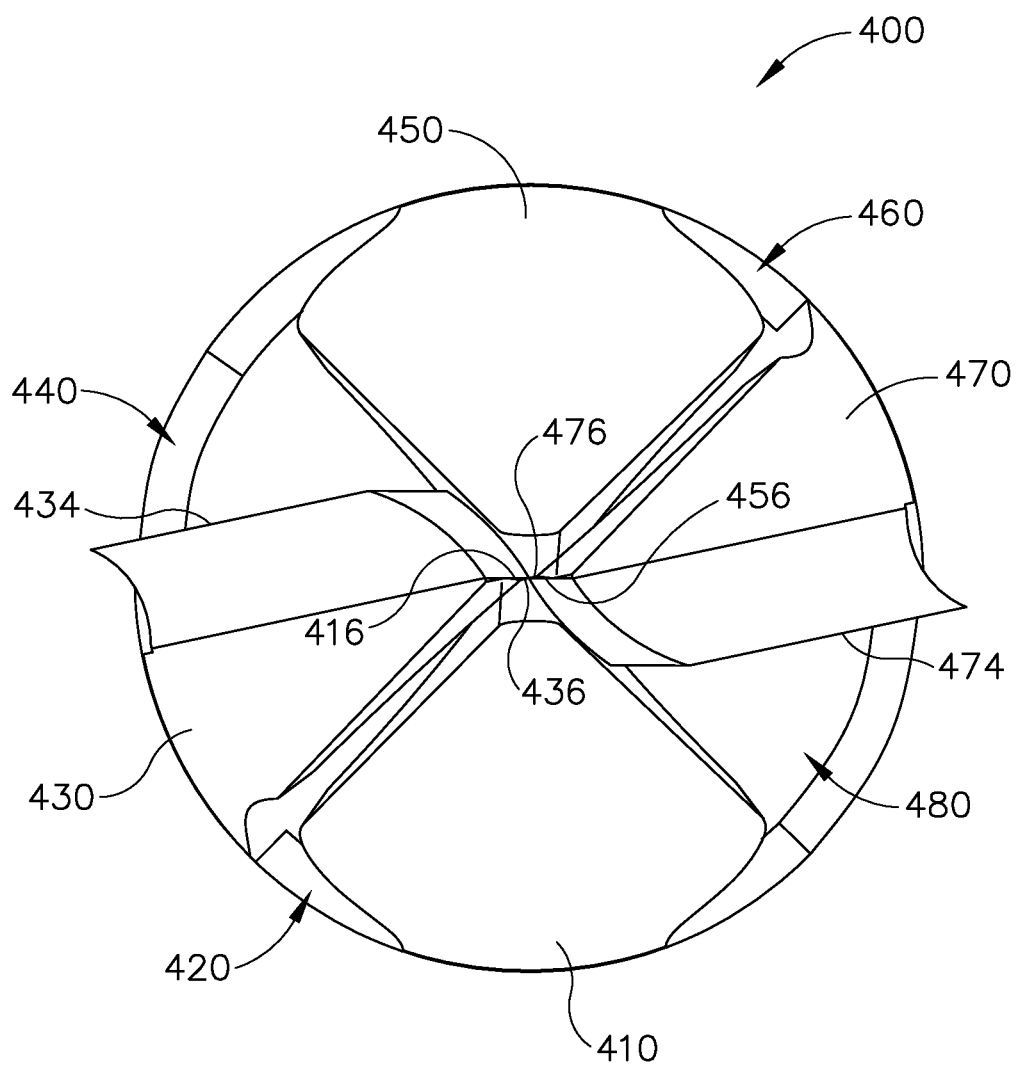
FIG. 22 depicts a distal end view of the dilator tube of FIG. 19, in the collapsed state.
Figure 23:
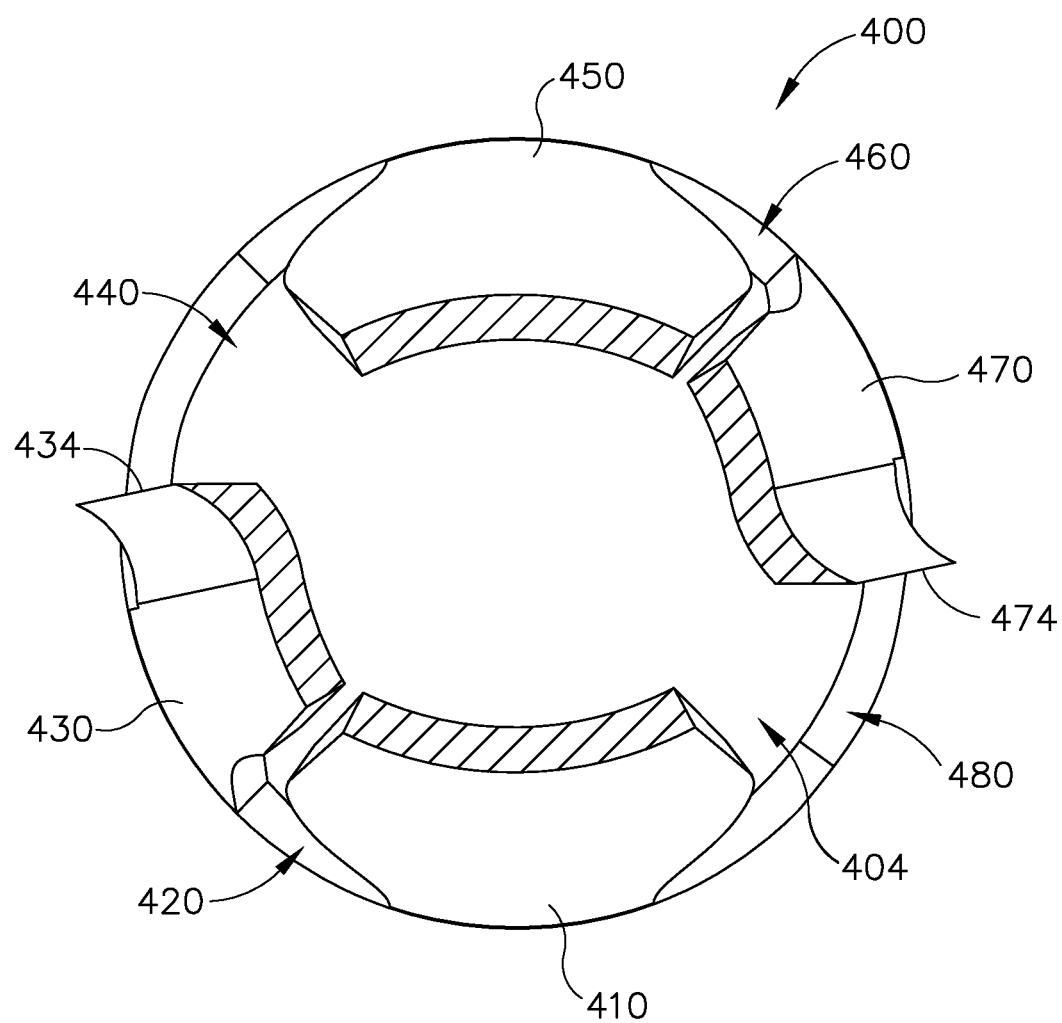
FIG. 23 depicts a cross-sectional view of the dilator tube of FIG. 19, taken along line 23-23 of FIG. 21.
Figure 24:
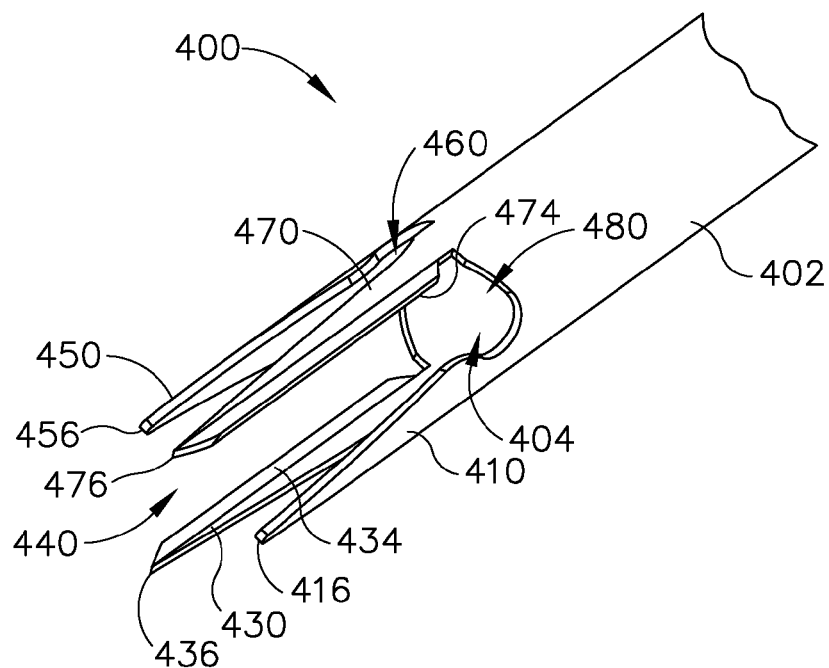
FIG. 24 depicts a perspective view of the dilator tube of FIG. 23, in an expanded state.
Figure 25:
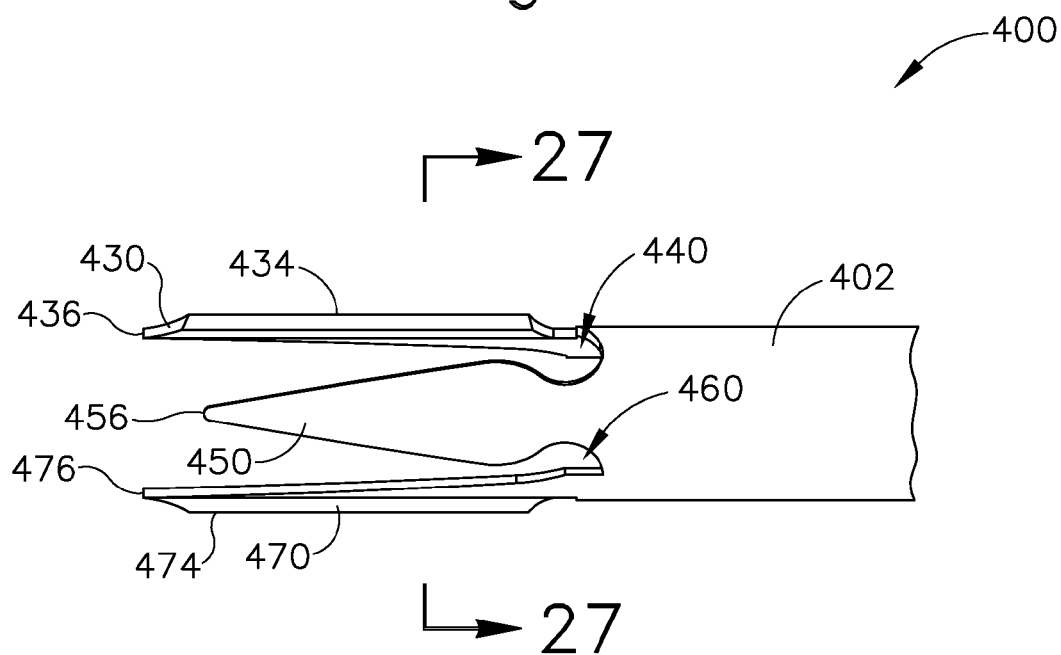
FIG. 25 depicts a side elevational view of the dilator tube of FIG. 19, in the expanded state.
Figure 26:
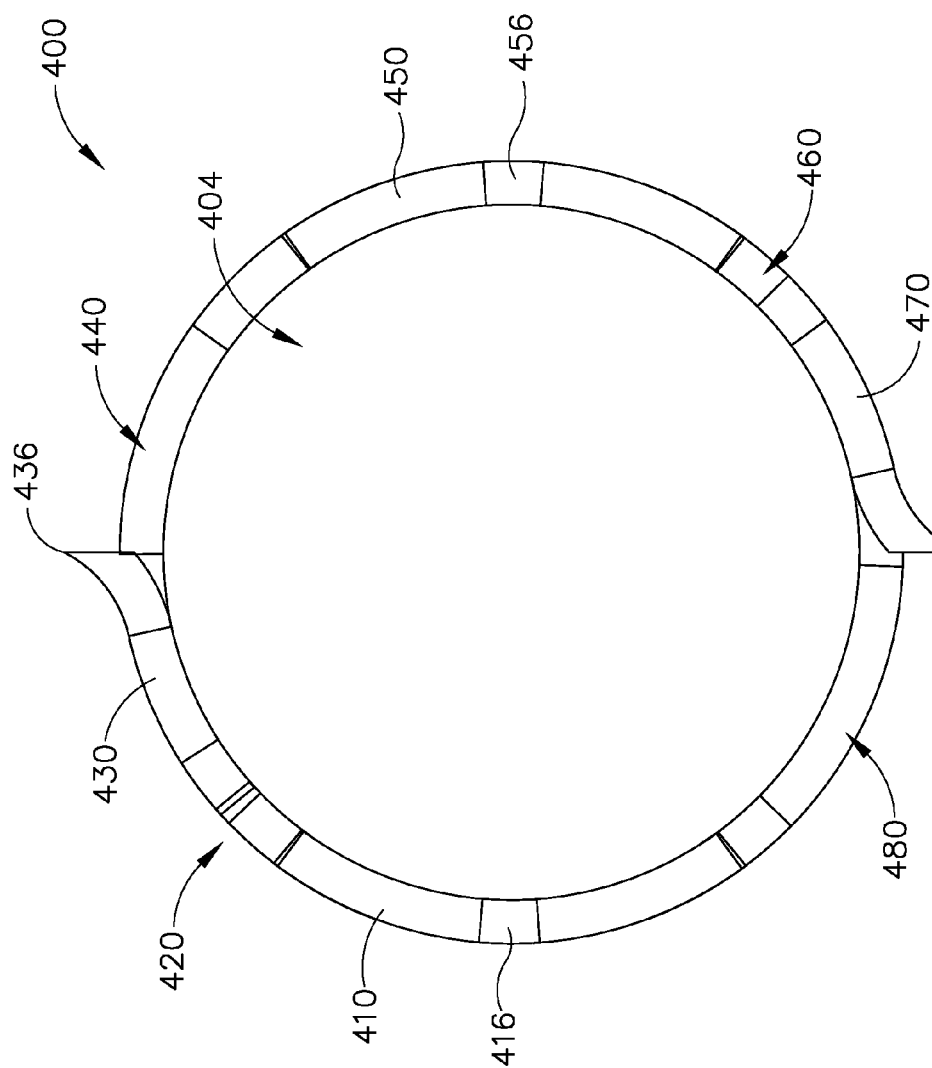
FIG. 26 depicts a distal end view of the dilator tube of FIG. 19, in the expanded state.
Figure 27:
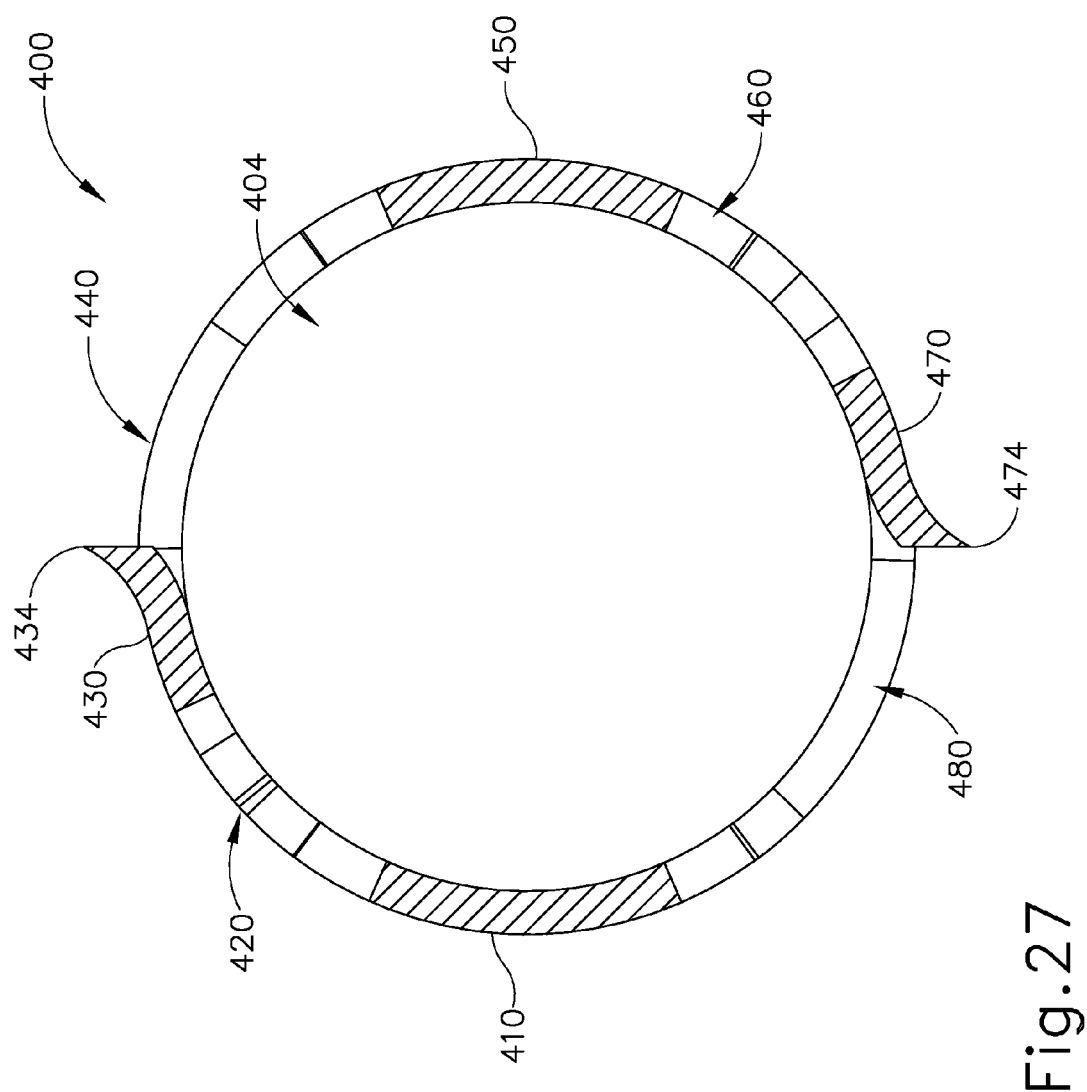
FIG. 27 depicts a cross-sectional view of the dilator tube of FIG. 19, taken along line 27-27 of FIG. 25.

FIGS. 17-18 show an exemplary alternative dilator tube (300) that may be used in place of both dilator tube (150) and piercer (180) described above. In some versions, dilator tube (300) may be secured to cam follower (152) as a substitute for dilator tube (150). Furthermore, piercer (180) and cam follower (182) may simply be omitted from versions of a PETDD (100) that has dilator tube (300). Dilator tube (300) of the present example comprises a tubular portion (302) and two leaves (310, 320). Leaf (310) is joined to tubular portion (302) by a living hinge (312). Leaf (320) is also joined to tubular portion (302) by a living hinge (322). A pair of longitudinally extending gaps (330) are defined between leaves (310, 320). These gaps (330) include rounded regions near hinges (312, 322). As can be seen in FIG. 17, leaves (310, 320) present a duckbill configuration when dilator (300) is in a collapsed state.

Leaves (310, 320) are resiliently biased to assume the collapsed, inwardly deflected positioning shown in FIG. 17. However, leaves (310, 320) may flex at hinges (312, 322) and thereby deflect outwardly to the positions shown in FIG. 18, such that leaves (310, 320) align along the cylindraceous path defined by tubular portion (302). In particular, as shield tube (160) is advanced distally through the interior of tubular portion (302), the distal end of shield tube (160) drives leaves (312, 322) outwardly to the position shown in FIG. 18.

The distal edge (314) of leaf (310) is generally round. However, the distal edge of leaf (320) includes a sharp point (324). Sharp point (324) projects distally relative to distal edge (314), such that dilator tube (300) leads with sharp point (324). It should be understood that, as dilator tube (300) is driven into the tympanic membrane (TM), sharp point (324) will pierce the tympanic membrane (TM) and thereby create a myringotomy incision like piercer (180) would create. In some instances, the incision created by sharp point (324) is in the form of a substantially straight line. After sharp point (324) creates the incision, leaves (310, 320) may be held in place within the incision while shield tube (160) is advanced distally through the interior of tubular portion (302), eventually driving leaves (310, 320) outwardly within the incision to dilate the incision. Dilator tube (300) and shield tube (160) may then be retracted proximally while pusher tube (170) remains longitudinally stationary, resulting in deployment of PE tube (1200) in the tympanic membrane (TM) as described above.

It should be understood that eliminating piercer (180) in the present example provides a more open fluid path within the lumen of pusher tube (170). In other words, without piercer (180) being positioned in the lumen of pusher tube (170), pusher tube is now more effective at providing fluid communication to the distal end of cannula (120). By way of example only, this larger fluid path may more effectively communicate suction to the distal end of cannula (120) in versions where PETDD (100) is coupled with a vacuum source. As noted above, such suction may be used to assist in drawing the tympanic membrane (TM) against tip (122) to improve apposition between the tympanic membrane (TM) and tip (122). In addition or in the alternative, suction may be used to remove fluid from the middle ear, and the larger fluid path provided by the elimination of piercer (180) may facilitate communication of the fluid proximally through the lumen of pusher tube (170). This suction of fluid may be performed after PE tube (1200) is deployed in the tympanic membrane (TM), with the fluid being drawn through passageway (1204) of the deployed PE tube (1200) and tip (122). Thus, PETDD (100) may be used to suction fluid from the middle ear immediately after deployment of PE tube (1200), instead of having to use a separate suction instrument.

B. Exemplary Dilator with Sharp Longitudinal Edges

FIGS. 19-27 show another exemplary alternative dilator tube (400) that may be used in place of both dilator tube (150) and piercer (180) described above. In some versions, dilator tube (400) may be secured to cam follower (152) as a substitute for dilator tube (150). Furthermore, piercer (180) and cam follower (182) may simply be omitted from versions of a PETDD (100) that has dilator tube (400). Dilator tube (400) of the present example comprises a tubular portion (402) and four leaves (410, 430, 450, 470). Leaf (410) is joined to tubular portion (402) by a living hinge (412). Leaf (430) is joined to tubular portion (402) by a living hinge (432). Leaf (450) is joined to tubular portion (402) by a living hinge (452). Leaf (470) is joined to tubular portion (402) by a living hinge (472). Longitudinally extending gaps (420, 440, 460, 480) are defined between leaves (410, 430, 450, 470). These gaps (420, 440, 460, 480) include rounded regions near hinges (412, 432, 452, 472). As can be seen in FIGS. 19-22, the distal ends of leaves (410, 430, 450, 470) converge when dilator (400) is in a collapsed state.

Leaves (410, 430, 450, 470) are resiliently biased to assume the collapsed, inwardly deflected positioning shown in FIGS. 19-23. However, leaves (410, 430, 450, 470) may flex at hinges (412, 432, 452, 472) and thereby deflect outwardly to the positions shown in FIGS. 24-27, such that leaves (410, 430, 450, 470) align along the cylindraceous path defined by tubular portion (402). In particular, as shield tube (160) is advanced distally through the interior of tubular portion (402), the distal end of shield tube (160) drives leaves (410, 430, 450, 470) outwardly to the position shown in FIGS. 24-27.

Leaves (410, 450) are on diametrically opposed sides of tubular portion (402) and have pointed yet generally blunt distal tips (416, 456). Leaves (430, 470) are on diametrically opposed sides of tubular portion (402), offset by 90 degrees from leaves (410, 450), and have sharp edges (434, 474) extending along their respective lengths, with sharp distal tips (436, 476). As best seen in FIGS. 22-23 and 26-27, leaves (430, 470) are bent such that sharp edges (434, 474) project outwardly. In the present example, each sharp edge (434, 474) is formed at the convergence of a curved surface and a radially extending surface of the corresponding leaf (430, 470). When leaves (410, 430, 450, 470) are driven outwardly to an expanded state as shown in FIGS. 24-27, the full lengths of sharp edges (434, 474) are positioned outside the outer diameter of tubular portion (402). Sharp distal tips (436, 476) project distally relative to blunt distal tips (416, 456), such that dilator tube (400) leads with sharp distal tips (436 476).

By way of example only, sharp edges (434, 474) and sharp distal tips (436, 476) may be formed in a laser cutting process. For instance, initial forms of leaves (410, 430, 450, 470) may be laser cut from tubular portion (402). Then, an edge of each leaf (430, 470) may be bent outwardly. The outwardly bent edges may then be laser cut again (e.g., along the same path as a diameter of tubular portion (402)) to form sharp edges (434, 474) and sharp distal tips (436, 476). Other suitable ways in which various features of dilator tube (400) may be formed will be apparent to those of ordinary skill in the art in view of the teachings herein. While four leaves (410, 430, 450, 470) are provided in the present example, it should be understood that any other suitable number of leaves may be used. For instance, dilator tube (400) may include more than two sharpened leaves (430, 470), regardless of how many unsharpened leaves (410, 450) are provided.

It should be understood that, as dilator tube (400) is driven into the tympanic membrane (TM), sharp distal tips (436, 476) will pierce the tympanic membrane (TM) and thereby create a myringotomy incision like piercer (180) would create. After sharp distal tips (436, 476) create the incision, leaves (410, 430, 450, 470) may be held in place within the incision while shield tube (160) is advanced distally through the interior (404) of tubular portion (402), eventually driving leaves (410, 430, 450, 470) outwardly within the incision to dilate the incision. Sharp edges (434, 474) may perform additional cutting of the tympanic membrane (TM) during this dilation step, effectively increasing the length of the incision created by sharp distal tips (436, 476). Dilator tube (400) and shield tube (160) may then be retracted proximally while pusher tube (170) remains longitudinally stationary, resulting in deployment of PE tube (1200) in the tympanic membrane (TM) as described above.

As with dilator tube (300) described above, eliminating piercer (180) in the present example provides a more open fluid path within the lumen of pusher tube (170). In other words, without piercer (180) being positioned in the lumen of pusher tube (170), pusher tube is now more effective at providing fluid communication to the distal end of cannula (120). By way of example only, this larger fluid path may more effectively communicate suction to the distal end of cannula (120) in versions where PETDD (100) is coupled with a vacuum source. As noted above, such suction may be used to assist in drawing the tympanic membrane (TM) against tip (122) to improve apposition between the tympanic membrane (TM) and tip (122). In addition or in the alternative, suction may be used to remove fluid from the middle ear, and the larger fluid path provided by the elimination of piercer (180) may facilitate communication of the fluid proximally through the lumen of pusher tube (170). This suction of fluid may be performed after PE tube (1200) is deployed in the tympanic membrane (TM), with the fluid being drawn through passageway (1204) of the deployed PE tube (1200) and tip (122). Thus, PETDD (100) may be used to suction fluid from the middle ear immediately after deployment of PE tube (1200), instead of having to use a separate suction instrument.

IV. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body;
   (b) a cannula extending distally from the body, wherein the cannula has an open distal end;
   (c) a cylindraceous member disposed within the cannula, wherein the cylindraceous member includes:
      (i) a tubular portion defining a longitudinal axis, wherein the tubular portion has a distal end and an outer diameter; and
      (ii) a plurality of leaves positioned at the distal end of the tubular portion, wherein the plurality of leaves are movable between a collapsed position and an expanded position,
      wherein the cylindraceous member is slidable relative to the cannula to selectively expose the plurality of leaves relative to the open distal end of the cannula,
      wherein a first leaf of the plurality of leaves has a sharp distal point configured to pierce a tympanic membrane and a longitudinally extending sharp edge configured to extend outside the outer diameter of the tubular portion in the expanded position.

2. The apparatus of claim 1, wherein the plurality of leaves includes four leaves.

3. The apparatus of claim 1, wherein a second leaf of the plurality of leaves has a sharp distal point configured to pierce a tympanic membrane and a longitudinally extending sharp edge configured to extend outside the outer diameter of the tubular portion in the expanded position.

4. The apparatus of claim 3, wherein the first leaf and the second leaf are positioned on diametrically opposed sides of the distal end of the tubular portion.

5. The apparatus of claim 3, wherein a third leaf of the plurality of leaves is angularly interposed between the first leaf and the second leaf.

6. The apparatus of claim 5, wherein the third leaf has a blunt distal tip.

7. The apparatus of claim 5, wherein a fourth leaf of the plurality of leaves is angularly interposed between the first leaf and the second leaf, and wherein the third leaf and the fourth leaf are positioned on diametrically opposed sides of the distal end of the tubular portion.

8. The apparatus of claim 7, wherein the fourth leaf has a blunt distal tip.

9. The apparatus of claim 8, wherein the third leaf has a blunt distal tip, and the blunt distal tips of the third and fourth leaves are proximal relative to the sharp distal points of the first and second leaves in the expanded position.

10. The apparatus of claim 1, wherein each leaf of the plurality of leaves is joined to the tubular portion by a living hinge.

11. The apparatus of claim 1, wherein each leaf of the plurality of leaves is resiliently biased to the collapsed position.

12. The apparatus of claim 1, wherein the longitudinally extending sharp edge of the first leaf is defined at the convergence of a curved surface of the first leaf and a radially extending surface of the first leaf.

13. The apparatus of claim 1, wherein the longitudinally extending sharp edge of the first leaf is configured to project parallel to the longitudinal axis of the tubular portion in the expanded position.

14. The apparatus of claim 1, further comprising a pusher member coaxially disposed within the cylindraceous member, wherein the pusher member is slidable relative to the cylindraceous member, and wherein the pusher member is operable to drive the plurality of leaves outwardly from the collapsed position to the expanded position.

15. The apparatus of claim 14, wherein the pusher member defines a lumen, wherein the apparatus further comprises a vacuum source in fluid communication with the lumen.

16. The apparatus of claim 1, further comprising a tympanostomy tube disposed within the cylindraceous member.

17. An apparatus comprising:
   (a) a body;
   (b) a cannula extending distally from the body, wherein the cannula has an open distal end;
   (c) a cylindraceous member disposed within the cannula, wherein the cylindraceous member comprises:
      (i) a tubular portion defining an outer diameter;
      (ii) a first leaf extending distally from the tubular portion, wherein the first leaf has a sharp distal tip and a longitudinally extending sharp edge; and
      (iii) a second leaf extending distally from the tubular portion,
      wherein the first leaf and the second leaf are movable between a collapsed position and an expanded position,
      wherein the first leaf and the second leaf converge in the collapsed position, and
      wherein the longitudinally extending sharp edge of the first leaf is configured to extend outside the outer diameter of the tubular portion in the expanded position.

18. The apparatus of claim 17, wherein the second leaf has a sharp distal tip and a longitudinally extending sharp edge.

19. An apparatus comprising:
   (a) a body;
   (b) a cannula extending distally from the body, wherein the cannula has an open distal end;
   (c) a cylindraceous member disposed within the cannula, wherein the cylindraceous member comprises:
      (i) a tubular portion defining a longitudinal axis, wherein the tubular portion has a distal end and an outer diameter; and
      (ii) a plurality of leaves movable between a collapsed position and an expanded position, wherein the plurality of leaves are positioned at the distal end of the tubular portion,
      wherein a first leaf of the plurality of leaves has a curved surface and a radially extending surface,
      wherein the curved surface and the radially extending surface converge to form a longitudinally extending sharp edge configured to extend outside the outer diameter of the tubular portion in the expanded position, and wherein the longitudinally extending sharp edge terminates in a sharp distal tip.

20. The apparatus of claim 19, wherein the second leaf has a curved surface and a radially extending surface, the curved surface and the radially extending surface converge to form a longitudinally extending sharp edge configured to extend outside the outer diameter of the tubular portion in the expanded position, and the longitudinally extending sharp edge terminates in a sharp distal tip.

* * * * *

UNITED STATES PATENT AND TRADEMARK OFFICE
CERTIFICATE OF CORRECTION

| | |
|---|---|
| PATENT NO. | : 9,681,891 B2 |
| APPLICATION NO. | : 13/804612 |
| DATED | : June 20, 2017 |
| INVENTOR(S) | : Bernard H. Andreas et al. |

It is certified that error appears in the above-identified patent and that said Letters Patent is hereby corrected as shown below:

On the Title Page

Item (72) Inventors, delete "Matthew D. Clopp" and insert --Mathew D. Clopp--.

Signed and Sealed this
Sixteenth Day of July, 2019

Andrei Iancu
*Director of the United States Patent and Trademark Office*